(12) United States Patent
Jackson et al.

(10) Patent No.: US 6,204,038 B1
(45) Date of Patent: Mar. 20, 2001

(54) DESATURASE ANTIGEN OF MYCOBACTERIUM TUBERCULOSIS

(75) Inventors: Mary Jackson; Brigitte Gicquel, both of Paris (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/422,662

(22) Filed: Oct. 22, 1999

Related U.S. Application Data

(62) Division of application No. 08/917,299, filed on Jul. 25, 1997, now Pat. No. 6,010,855.
(60) Provisional application No. 60/022,713, filed on Jul. 26, 1996.

(51) Int. Cl.[7] .............................. C12N 9/02; A61K 38/44; A61K 39/04
(52) U.S. Cl. ..................... 435/189; 424/94.4; 424/185.1; 424/248.1
(58) Field of Search ........................ 435/189; 424/248.1, 424/185.1, 94.4; 536/23.2

(56) References Cited

PUBLICATIONS

Philipp et al. "An integrated map of the genome of the tubercle bacillus, *Mycobacterium tuberculosis* H37Rv, . . . " Proc. Natl. Acad. Sci. U. S. A. 93, 3132–3137, Apr. 1996.*

Jackson et al. "*Mycobacterium tuberculosis* Des protein: an immunodominant . . . " Infection and Immunity 65, 2883–2889, Apr. 1996.*

Lim et al., "Identification of *Mycobacterium tuberculosis* DNA Sequences Encoding Exported Proteins by Using phoA Gene Fusions", *J. Bacteriology*, vol. 177, No. 1, pp 59–65 (Jan. 1995).

* cited by examiner

*Primary Examiner*—Nashaat T. Nashed
(74) *Attorney, Agent, or Firm*—Finnegan, Henderson, Farabow, Garrett & Dunner, L.L.P.

(57) ABSTRACT

The present invention relates to the isolation of a new gene, des, which encodes a *M. tuberculosis* protein named DES. The des gene appears to be conserved among different Mycobacteria species. The amino acid sequence of the DES protein contains two sets of motifs that are characteristic of the active sites of enzymes from the class II diiron-oxo protein family. Among this family of proteins, DES shares significant homology with soluble stearoyl-ACP desaturases. DES is a highly antigenic protein, which is recognized by human sera from patients infected with *M. tuberculosis* and *M. leprae* but not by sera from tuberculous cattle. Thus, the DES protein provides a useful tool for the serodiagnostic analysis of tuberculosis.

3 Claims, 12 Drawing Sheets

```
  1 GATCATCATCGGCCGGCTGCCGCGGCCAGGGCGCCGACACCGGCGAGTGCGGGCGCGAGGATCGGCCCCCAC
 71 CAGTTCGGCAGCTGCGTGTCGATGCGCTCCACAATCCCGGAAACAGCTCGACCATTACCTCCTCAATAT
141 GAGCCTCGAAAACTTGCCCGCTGCGCGGGCTCGTGTGGTCGTGAGCGCACACAACTGTTAGCTGACCAGC
211 AGGATCGGGCGCTCTTACCGGTCTCGTTCACCGCATATCTGAACGGAAGACGGCTGGAGCCACCCGCAAGCAAT
281 TCATCGACTACTGCGTCAACATGTTGCTCAGCACCGCCACCTACGCACCGCACCGCGAGCGGGGAGA
351 ATCCGAACACTCCATCCGCCGGGCCGCACAACTGAGGACGACTGGGTTCACCCCACGCGGCCACCGG
421 CGCCCGCCGATGCCAGCATCCTGCCCGCTGCTGCCAGCTCAACATGCCGCGGCGAAGCCCAAACTTGATGC
491 TACCGAGAGACACAGATATATTGACTGCAACCATTAGACACAGATAACTGAGGCGCCATGTCAGCCAAG
                                                             M S A K
561 CTGACCGACCTCGCAGCTGCTCCAGCGAACCGGTCTGCTGAGAAGTACCTGAACGGCACCTGAGCA
      L T D L Q L L H E L E P V V E K Y L N R H L S M
631 TGCACAAGCCCTGAACCCGACGACTACATCCCGGTCTCGGACGGAAGAACTACGCGCTCGGCGG
      H K P W N P H D Y I P W S D G K N Y Y A L G G
701 GCAGGATTGGGACCCCGACCAGAGCAAGCTTTCTGATGTCGCCCAGGTGGCCGATGGTGCAGAACCTGGTC
      Q D W D P D Q S K L S D V A Q V A M V Q N L V
771 ACCGAGGACAACAACTGCCCGTCGTATCACCGCGAGATCGCCGATGAACATGGCATGGACGGCGCTGGGGGC
      T E D N L P S Y H R E I A M N M G M D G A W G Q
841 AGTGGGTCAACCGTTGGACCGCCGAGAATCGGCCACGCGACTGCGCGACTACCTGGTGGTGAC
      W V N R W T A E E N R H G I A L R D Y L V V T
911 CCGATCGGTCGACCCTGTCGAGTTGGAGAAACTTCGCCTCGAGGTAGTCAACCGGGGCTTCAGCCCAGGC
      R S V D P V E L E K L R L E V V N R G F S P G
```

```
 981  CAAAAACCACCAGGGCCACTATTTCGGGAGAGCCTCACCGACTCCGTCCTCTATGTCAGTTTCCAGGAAC
       Q  N  H  Q  G  H  Y  F  A  E  S  L  T  D  S  V  L  Y  V  S  F  Q  E  L

1051  TGGCAACCCGGATTTCGCACCCGCAATACCGGCAAGGCATGTAACGACCCCGTCGCCGACCAGCTCATGGC
       A  T  R  I  S  H  R  N  T  G  K  A  C  N  D  P  V  A  D  Q  L  M  A

1121  CAAGATCTCGGCAGACGAGAATCTGCACATGATCTTCTACCGCGACGTCAGCGAGGCCGCGTTCGACCTC
       K  I  S  A  D  E  N  L  H  M  I  F  Y  R  D  V  S  E  A  A  F  D  L

1191  GTGCCAACCAGGCCATGAAGTCGCTGCACTTCCAGATGCCCGGCTTCCAAGTAC
       V  P  N  Q  A  M  K  S  L  H  L  I  L  S  H  F  Q  M  P  G  F  Q  V  P

1261  CCGAGTTCCGGCGCAAAGCCGTGGTCATCGCCGTGGTGTCTACGACCCGCGCATCCACCTGACGA
       E  F  R  R  K  A  V  V  I  A  V  G  G  V  Y  D  P  P  R  I  H  L  D  E

1331  AGTCGTCATGCCGGTACTGAAGAAAATGGTGTATCTTCGAGGACCCGAGGACTTCACCGGCGAGGGGCTAAG
       V  V  M  P  V  L  K  K  W  C  I  F  E  R  E  D  F  T  G  E  G  A  K

1401  CTGCGCGACGAGCTGGCCCTGGTGATCAAGGACCTCGAGCTGGCCTGCGACAAGTTCGAGGTGTCCAAGC
       L  R  D  E  L  A  L  V  I  K  D  L  E  L  A  C  D  K  F  E  V  S  K  Q

1471  AACGCCAACTCGACCGGGAAGCCGTACGGCAAGAAGGTCAGCGCACACGAGCTGCATAAAACCGCTGG
       R  Q  L  D  R  E  A  R  T  G  K  K  V  S  A  H  E  L  H  K  T  A  G

1541  CAAACTGGCCATGAGCCGTCGTTAGCCCGACGATGAGCAGGAGCGCGATGAGCAGGAGGCGGG
       K  L  A  M  S  R  R  *  (SEQ ID NO. 4)

1611  CAATCCAACCAGCCCGGCGACGATGCAGAGCGCGCAGCGCGATGAGCAGGAGGTGGGCAATCCAACCCA

1681  GCCCGGCGTTG    (SEQ ID NO. 3)
```

```
                           ───────── Fe A site ──────────
         ─── B Helix ───                              ─── C Helix ───

Ribonucleotide reductases v01555  049 EFYKFLFTFL AMA E KLVNFN IDELVTSFES HDIDHYYTEQKAM ENVH GETYA 099 (SEQ ID NO.6)
k02672  072 IFISNLKYQT LL D SIQGRSP NVALLPLISI PELETWVETWAFS ETIH SRSYT 123 (SEQ ID NO.7)

Hydrocarbon hydroxylases m58499  102 ETMKVVSNFL EVG E YNAIAA TGMLWDSAQA AEQKNGYLAQVL D EIRH THQCA 152 (SEQ ID NO.8)
x55394  102 ETMKVISNFL EVG E YNAIAA SAMLWDSATA AEQKNGYLAQVL D EIRH THQCA 152 (SEQ ID NO.9)
m60276  097 NALKLFLTAV SPL E YQAFQG FSRVGRQFSG AGARVACQMQAI D ELRH VQTQV 147 (SEQ ID NO.10)
m65106  092 STLKSHYGAI AVG E YAAVTG EGRMARFSKA PGNRNMATFGMM D ELRH GQLQL 142 (SEQ ID NO.11)

Stearoyl-ACP-desaturases m59857  133 LVGDMITEEA LPTYQTMLNT LDGVRDETGA SPTSWAIWTRAWTA E ENRH GDLLN 184 (SEQ ID NO.12)
m59858  133 LVGDMITEEA LPTYQTMLNT LDGVRDETGA SPTPWAIWTRAWTA E ENRH GDLLN 184 (SEQ ID NO.13)
m61109  133 LVGDMITEEA LPTYQTMLNT LDGVRDETGA SLTPWAVWTRAWTA E ENRH GDLLH 184 (SEQ ID NO.14)
x62898  136 LVGDMITEEA LPTYQTMLNT LDGAKDETGA SPTSWAVWTRAWTA E ENRH GDLLN 187 (SEQ ID NO.15)
x60978  135 LVGDMITEEA LPTYQTMLNT LDGVRDETGA SPTSWAIWTRAWTA E ENRH GDLLN 186 (SEQ ID NO.16)
m91238  130 LIGDMITEEA LPTYQTMLNT LDGVRDETGA TVTPWAIWTRAWTA E ENRH GDLLN 181 (SEQ ID NO.17)
x70962  133 LVGDMITEEA LPTYQTMINT LDGVRDETGA SLTPWAIWTRAWTA E ENRH GDLLN 184 (SEQ ID NO.18)
m93115  121 LVGDMITEEA LPTYMSMLNR CDGIKDDTGA QPTSWATWTRAWTA E ENRH GDLLN 172 (SEQ ID NO.19)

M. tuberculosis DES protein

Mtb.des  062 SDVAQVAMVQ NLVTEDNLPS YHREIAMNMG MDGAWGQWVNRWTA E ENRH GIALR 115 (SEQ ID NO.20)
```

FIG. 3A

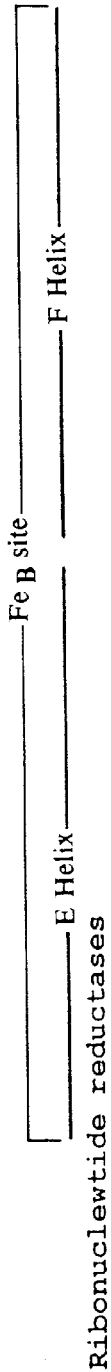

```
                    ———— E Helix ————                              ———— Fe_B site ————
                                                                                              ———— F Helix ————
Ribonuclewtide reductases v01555   145 EKILVFLLI E GIFFISSFYS IALLRVRGLM PGICLANNYISR D ELLH TRAAS 196 (SEQ ID NO.21)
k02672   195 LCLMSVNAL E AIRFYVSFAC SFAFAERELM EGNAKIIRLIAR D EALH LTGTQ 246 (SEQ ID NO.22)

Hydrocarbon hydroxylases m58499   200 CSLNLQLVG E ACFTNPLIVA VTEWAAANGD EITPTVFLSIET D ELRH MANGY 251 (SEQ ID NO.23)
x55394   200 CSVNLQLVG D TCFTNPLIVA VTEWAIGNGD EITPTVFLSVET D ELRH MANGY 251 (SEQ ID NO.24)
m60276   191 FLTAVSFSF E YVLTNLLFVP EMSGAAYNGD MATVTFGFSAQS D EARH MTLGL 242 (SEQ ID NO.25)
m65106   188 VAIMLTFSF E TGFTNMQFLG LAADAAEAGD YTFANLISSIQT D ESRH AQQGG 239 (SEQ ID NO.26)

Stearoyl-ACP-desaturases m59857   219 YLGFIYTSFQ E RATFISHGN TARQAKEHGD IKLAQICGTIAA D EKRH ETAYT 270 (SEQ ID NO.27)
m59858   219 YLGFIYTSFQ E RATFISHGN TARLAKEHGD IKLAQICGTITA D EKRH ETAYT 270 (SEQ ID NO.28)
m61109   219 YLGFIYTSFQ E RATFVSHGN TARHAKDHGD VKLAQICGTIAS D EKRH ETAYT 270 (SEQ ID NO.29)
x62898   222 YLGFVYTSFQ E RATFVSHGN SARLAKEHGD LKMAQICGIIAS D EKRH ETAYT 273 (SEQ ID NO.30)
x60978   221 YLGFIYTSFQ E RATFISHGN TARQAKEHGD LKLAQICGTIAA D EKRH ETAYT 272 (SEQ ID NO.31)
m91238   216 YLGFVYTSLR K GVTFVSHGN TARLAKEHGD MKLAQICGSIAA D EKRH ETAYT 267 (SEQ ID NO.32)
x70962   219 YLGFIYTSFQ E RATFISHGN TARLAKDHGD MKLAQICGIIAA D EKRH ETAYT 219 (SEQ ID NO.33)
m93115   207 YMGFIYTSFQ E RATFISHAN TAKLAQHYGD KNLAQVCGNIAS D ATAYT ATAYT 258 (SEQ ID NO.34)

M. tuberculosis DES protein

Mtb.des  157 TDSVLYVSFQ E LATRISHRN TGKACNDPVA DQLMAK...ISA D ENLH MIFYR 205 (SEQ ID NO.35)
```

FIG. 3B

—□— Average of tuberculous patients
(*M. tuberculosis*) (15 individuals)

—◇— Average of tuberculous patients
(*M. bovis*) (5 individuals)

----O---- Average of non-tuberculous patients
(24 individuals)

```
  1  GATCATCATCGGGCCGGCTGCCGCGCCAGGGGCGCCGACACCGGCGAGTGCGGGGCGGAGGATCGGCCCCCAC
 71  CAGTTCGGCAGCTGCCGTGTCGATGCGCTCCACAATCCCGGGAAACAGCTCGACCATTACCTCCTCAATAT
141  GAGCCTCGAAAAACTTGCCGCTGTGCGGGCGTCGTGGTGAGCGCACACAACAACTGTTAGCTGACCAGC
211  AGGATCGGGCGCTCTTACCGGTCTGTTCACCGCATATCTGAACGGACGGCTGGGAGCCACCCGCAAGCAAT
281  TCATCGACTACTGCGTCAACATGTGCTCAGCACCGCCACCTACGCACCGCGAGCGGGGAGA
351  ATCCGAACACTCCATCCCAGCCGGGCCGCACAACTGAGGACGACTGGGTTCACCCCACGCGGCCACCGG
                                                                              -35
421  GGCCCGCCGATGCCAGCATCCTGCCCGCTGCTGGCAGCTCAACATGCCGCGCGAAGCCCAAACTTGATGC
           -10                    +1
491  TACCGAGAGACACAGATATATTGACTGCAACATTAGACACAGATAACTGGAGGCGCCATGTCAGCCAAG
                                                                   M  S  A  K
561  CTGACCGACCTGCAGCTGCTGCACGAACTTGAACCGGTCGTCGAGAAGTACCTGAACCGGCACCTGAGCA
      L  T  D  L  Q  L  L  H  E  L  E  P  V  V  E  K  Y  L  N  R  H  L  S  M
631  TGCACAAGCCCTGGAACCCGCACGACTACATCCCGTGGTCGGACGGGAAGAACTACTACGCGCTCGGCGG
      H  K  P  W  N  P  H  D  Y  I  P  W  S  D  G  K  N  Y  Y  A  L  G  G
701  GCAGGATTGGGACCCGGACCAGAGCAAGCTTTCTGATGTCGCCCAGGTGGCGATGGTGCAGAACCTGGTC
      Q  D  W  D  P  D  Q  S  K  L  S  D  V  A  Q  V  A  M  V  Q  N  L  V
771  ACCGAGGACAACCTGCCGTCGTATCACCGCGAGATCGCGATGAACATGGGCATGGACGGTGGGGGC
      T  E  D  N  L  P  S  Y  H  R  E  I  A  M  N  M  G  M  D  G  A  W  G  Q
```

```
 841  AGTGGGTCAACCGTTGGACCGCCGAGGAGAATCGGCACGGCATCGCGCTGCGCGACTACCTGGTGGTGAC
        W  V  N  R  W  T  A  E  E  N  R  H  G  I  A  L  R  D  Y  L  V  V  T
 911  CCGATCGGTCGACCCTGTCGAGTTGGAGAAACTTCGCCTCGAGTAGTCAACCGGGCTTCAGCCCAGGC
        R  S  V  D  P  V  E  L  E  K  L  R  L  E  V  V  N  R  G  F  S  P  G
 981  CAAAAACCACCAGGGCCACTATTTCGCGGAGAGCCTCCGACTCCGTCCTCTATGTCAGTTTCCAGGAAC
        Q  N  H  Q  G  H  Y  F  A  E  S  L  T  D  S  V  L  Y  V  S  F  Q  E  L
1051  TGGCAACCCGGATTCGCACCGGCAATACCGGCAAGGCATGTAACGACCCGGTCGCCGACCAGCTCATGGC
        A  T  R  I  S  H  R  N  T  G  K  A  C  N  D  P  V  A  D  Q  L  M  A
1121  CAAGATTCTCGGCACAGACGAGAATCTGCACATGATCTTCTACCGCGACGTCAGCGAGGCCGCGTTCGACCTC
        K  I  S  A  D  E  N  L  H  M  I  F  Y  R  D  V  S  E  A  A  F  D  L
1191  GTGCCCAACCAGGCCATGAAGTCGCTGCACCTGATTTTGAGCCACTTCCAGATGCCCGGCTTCCAAGTAC
        V  P  N  Q  A  M  K  S  L  H  L  I  L  S  H  F  Q  M  P  G  F  Q  V  P
1261  CCGAGTTCCGGCGCAAAGCCGTGGTCATCGCCGTGGTGTCTACGACCCGCCGCATCCACCTCGACGA
        E  F  R  R  K  A  V  V  I  A  V  G  G  V  Y  D  P  P  R  I  H  L  D  E
1331  AGTCGTCATGCCGGTACTGAAGAAATGGTGTATCTTCGAAGGACCTGGACAAGTTCGAGGTGTCCAAGC
        V  V  M  P  V  L  K  K  W  C  I  F  E  R  E  D  F  T  G  E  G  A  K
1401  CTGGCGGCGACGAGCTGGCCCTGGTGATCAAGGACCTGGAGCTGGCGACAAGTTCGAGGTGTCCAAGC
        L  R  D  E  L  A  L  V  I  K  D  L  E  L  A  C  D  K  F  E  V  S  K  Q
1471  AACGCCAACTCGACCGGGAAGCCCGTACGGGCAAGAAGGTCAGCGCCACACGAGCTGCATAAAACCGCTGG
        R  Q  L  D  R  E  A  R  T  G  K  K  V  S  A  H  E  L  H  K  T  A  G
1541  CAAACTGGCGATGAGCCGTCGTTAGCCGGCGACGATGCAGAGCGCGCGCGATGAGC  (SEQ ID NO.36)
        K  L  A  M  S  R  R  *  (SEQ ID NO.37)
```

| Strain or plasmid | Relevant characteristics |
|---|---|
| E. coli DH5α | F/endA1 hsdR17(r$_k$⁻m$_k$⁻) supE44 thi-1 recA1 gyrA (Nal$^r$) relA1 Δ(lacZYA-argF)U169 deoR (Φ80fdlacΔ(lacZ)M15) |
| E. coli BL21(DE3)pLysS | F- ompT hsdS$_B$(r$_B$⁻m$_B$⁻; an E. coli B strain) with a λ prophage carrying the T7 RNA polymerase gene. |
| M. smegmatis mc²155 | High transformation mutant of M. smegmatis ATCC607 |
| M. tuberculosis H37Rv | Virulent strain of mycobacterium originally isolated from tuberculosis patient |
| pBluescript KS- | Phagemid derived from pUC19 cloning vector |
| pYUB18 | (Km)$^R$ shuttle vector used for the construction of a M. tuberculosis cosmid library |
| pJEM11 | E.coli-mycobacterium shuttle vector carrying a truncated phoA gene |
| pET14b | pBR322 derivative containing a T7 promoter for expression of target DNAs. |
| pExp421 | pJEM11 vector carrying the 1.1 kb insert from the des-PhoA fusion |
| pBS-des | pBluescript KS- vector carrying the EcoRV 4.5kb insert containing the des gene |
| pET-des | pET14b vector carrying the (JD8-JD9)des PCR amplification product |

FIG. 8

1. Pool of sera from tuberculous cattle
2. Pool of sera from lepromatous leprosy patients
3. Individual sera from *M. bovis*-infected tuberculous patients
4. Individual sera from *M. tuberculosis*-infected tuberculous patients

SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
      (A) LENGTH: 33 base pairs
      (B) TYPE: nucleic acid
      (C) STRANDEDNESS: single
      (D) TOPOLOGY: not relevant (ii) MOLECULE TYPE: other nucleic acid
      (A) DESCRIPTION: /desc = "NUCLEIC ACID"

(xi) SEQUENCE DESCRIPTION: SEQ ID NO: 1:

CGGCATATGT CAGCCAAGCT GACCGACCTG CAG      33

(2) INFORMATION FOR SEQ ID NO: 2:

(i) SEQUENCE CHARACTERISTICS:
      (A) LENGTH: 33 base pairs
      (B) TYPE: nucleic acid
      (C) STRANDEDNESS: single
      (D) TOPOLOGY: not relevant (ii) MOLECULE TYPE: other nucleic acid
      (A) DESCRIPTION: /desc = "NUCLEIC ACID"

(xi) SEQUENCE DESCRIPTION: SEQ ID NO: 2:

CCGGGATCCC GCGCTCGCCG CTCTGCATCG TCG      33

(2) INFORMATION FOR SEQ ID NO: 3:

(i) SEQUENCE CHARACTERISTICS:
      (A) LENGTH: 1691 base pairs
      (B) TYPE: nucleic acid
      (C) STRANDEDNESS: single
      (D) TOPOLOGY: not relevant (ii) MOLECULE TYPE: other nucleic acid
      (A) DESCRIPTION: /desc = "NUCLEIC ACID"

(ix) FEATURE:

(A) NAME/KEY: CDS
(B) LOCATION: 549..1562

(xi) SEQUENCE DESCRIPTION: SEQ ID NO: 3:

```
GATCATCATC GGCCGGCTGC CGCGCAGGGC GCCGACACCG GCGAGTGCGG GCGCGAGGAT      60

CGGCCCCCAC CAGTTCGGCA GCTGCGTGTC GATGCGCTCC ACAATCCCGG GAAACAGCTC     120

GACCATTACC TCCTCAATAT GAGCCTCGAA AAACTTGCCG CTGTGCGCGG CGTCGTGGTG     180

AGCGCACACA ACAACTGTTA GCTGACCAGC AGGATCGGCG CTCTTACCGG TCTGTTCACC     240

GCATATCTGA ACGGACGGCT GGGAGCCACC CGCAAGCAAT TCATCGACTA CTGCGTCAAC     300

ATGTTGCTCA GCACCGCCGC CACCTACGCA CCGCACCGCG AGCGGGGAGA ATCCGAACAC     360

TCCATCCCAG CCGGGCCGCA CAACTGAGGA CGACTGGGGT TCACCCCACG CGGCCACCGG     420

GGCCCGCCGA TGCCAGCATC CTGCCCGCTG CTGGCAGCTC AACATGCCGC GCGAAGCCCA     480

AACTTGATGC TACCGAGAGA CACAGATATA TTGACTGCAA CCATTAGACA CAGATAACTG     540

GAGGCGCC ATG TCA GCC AAG CTG ACC GAC CTG CAG CTG CTG CAC GAA CTT     590
         Met Ser Ala Lys Leu Thr Asp Leu Gln Leu Leu His Glu Leu
           1               5                  10

GAA CCG GTC GTC GAG AAG TAC CTG AAC CGG CAC CTG AGC ATG CAC AAG         638
Glu Pro Val Val Glu Lys Tyr Leu Asn Arg His Leu Ser Met His Lys
 15              20                  25                  30

CCC TGG AAC CCG CAC GAC TAC ATC CCG TGG TCG GAC GGG AAG AAC TAC         686
Pro Trp Asn Pro His Asp Tyr Ile Pro Trp Ser Asp Gly Lys Asn Tyr
                 35                  40                  45

TAC GCG CTC GGC GGG CAG GAT TGG GAC CCC GAC CAG AGC AAG CTT TCT         734
Tyr Ala Leu Gly Gly Gln Asp Trp Asp Pro Asp Gln Ser Lys Leu Ser
                 50                  55                  60

GAT GTC GCC CAG GTG GCG ATG GTG CAG AAC CTG GTC ACC GAG GAC AAC         782
Asp Val Ala Gln Val Ala Met Val Gln Asn Leu Val Thr Glu Asp Asn
             65                  70                  75

CTG CCG TCG TAT CAC CGC GAG ATC GCG ATG AAC ATG GGC ATG GAC GGC         830
Leu Pro Ser Tyr His Arg Glu Ile Ala Met Asn Met Gly Met Asp Gly
             80                  85                  90

GCG TGG GGG CAG TGG GTC AAC CGT TGG ACC GCC GAG GAG AAT CGG CAC         878
Ala Trp Gly Gln Trp Val Asn Arg Trp Thr Ala Glu Glu Asn Arg His
 95                 100                 105                 110

GGC ATC GCG CTG CGC GAC TAC CTG GTG GTG ACC CGA TCG GTC GAC CCT         926
Gly Ile Ala Leu Arg Asp Tyr Leu Val Val Thr Arg Ser Val Asp Pro
                115                 120                 125

GTC GAG TTG GAG AAA CTT CGC CTC GAG GTA GTC AAC CGG GGC TTC AGC         974
Val Glu Leu Glu Lys Leu Arg Leu Glu Val Val Asn Arg Gly Phe Ser
                130                 135                 140

CCA GGC CAA AAC CAC CAG GGC CAC TAT TTC GCG GAG AGC CTC ACC GAC        1022
Pro Gly Gln Asn His Gln Gly His Tyr Phe Ala Glu Ser Leu Thr Asp
            145                 150                 155

TCC GTC CTC TAT GTC AGT TTC CAG GAA CTG GCA ACC CGG ATT TCG CAC        1070
Ser Val Leu Tyr Val Ser Phe Gln Glu Leu Ala Thr Arg Ile Ser His
            160                 165                 170

CGC AAT ACC GGC AAG GCA TGT AAC GAC CCC GTC GCC GAC CAG CTC ATG        1118
Arg Asn Thr Gly Lys Ala Cys Asn Asp Pro Val Ala Asp Gln Leu Met
175                 180                 185                 190

GCC AAG ATC TCG GCA GAC GAG AAT CTG CAC ATG ATC TTC TAC CGC GAC        1166
Ala Lys Ile Ser Ala Asp Glu Asn Leu His Met Ile Phe Tyr Arg Asp
                195                 200                 205

GTC AGC GAG GCC GCG TTC GAC CTC GTG CCC AAC CAG GCC ATG AAG TCG        1214
Val Ser Glu Ala Ala Phe Asp Leu Val Pro Asn Gln Ala Met Lys Ser
                210                 215                 220
```

```
CTG CAC CTG ATT TTG AGC CAC TTC CAG ATG CCC GGC TTC CAA GTA CCC      1262
Leu His Leu Ile Leu Ser His Phe Gln Met Pro Gly Phe Gln Val Pro
        225                 230                 235

GAG TTC CGG CGC AAA GCC GTG GTC ATC GCC GTC GGG GGT GTC TAC GAC      1310
Glu Phe Arg Arg Lys Ala Val Val Ile Ala Val Gly Gly Val Tyr Asp
    240                 245                 250

CCG CGC ATC CAC CTC GAC GAA GTC GTC ATG CCG GTA CTG AAG AAA TGG      1358
Pro Arg Ile His Leu Asp Glu Val Val Met Pro Val Leu Lys Lys Trp
255                 260                 265                 270

TGT ATC TTC GAG CGC GAG GAC TTC ACC GGC GAG GGG GCT AAG CTG CGC      1406
Cys Ile Phe Glu Arg Glu Asp Phe Thr Gly Glu Gly Ala Lys Leu Arg
            275                 280                 285

GAC GAG CTG GCC CTG GTG ATC AAG GAC CTC GAG CTG GCC TGC GAC AAG      1454
Asp Glu Leu Ala Leu Val Ile Lys Asp Leu Glu Leu Ala Cys Asp Lys
        290                 295                 300

TTC GAG GTG TCC AAG CAA CGC CAA CTC GAC CGG GAA GCC CGT ACG GGC      1502
Phe Glu Val Ser Lys Gln Arg Gln Leu Asp Arg Glu Ala Arg Thr Gly
    305                 310                 315

AAG AAG GTC AGC GCA CAC GAG CTG CAT AAA ACC GCT GGC AAA CTG GCG      1550
Lys Lys Val Ser Ala His Glu Leu His Lys Thr Ala Gly Lys Leu Ala
320                 325                 330

ATG AGC CGT CGT TAGCCCGGCG ACGATGCAGA GCGCGCAGCG CGATGAGCAG          1602
Met Ser Arg Arg
335

GAGGCGGGCA ATCCAACCCA GCCCGGCGAC GATGCAGAGC GCGCAGCGCG ATGAGCAG      1662

GGTGGGCAAT CCAACCCAGC CCGGCGTTG                                      1691

(2) INFORMATION FOR SEQ ID NO: 4:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO: 4:

Met Ser Ala Lys Leu Thr Asp Leu Gln Leu Leu His Glu Leu Glu Pro
 1               5                  10                  15

Val Val Glu Lys Tyr Leu Asn Arg His Leu Ser Met His Lys Pro Trp
            20                  25                  30

Asn Pro His Asp Tyr Ile Pro Trp Ser Asp Gly Lys Asn Tyr Tyr Ala
        35                  40                  45

Leu Gly Gly Gln Asp Trp Asp Pro Asp Gln Ser Lys Leu Ser Asp Val
    50                  55                  60

Ala Gln Val Ala Met Val Gln Asn Leu Val Thr Glu Asp Asn Leu Pro
65                  70                  75                  80

Ser Tyr His Arg Glu Ile Ala Met Asn Met Gly Met Asp Gly Ala Trp
                85                  90                  95

Gly Gln Trp Val Asn Arg Trp Thr Ala Glu Glu Asn Arg His Gly Ile
            100                 105                 110

Ala Leu Arg Asp Tyr Leu Val Val Thr Arg Ser Val Asp Pro Val Glu
        115                 120                 125

Leu Glu Lys Leu Arg Leu Glu Val Val Asn Arg Gly Phe Ser Pro Gly
    130                 135                 140

Gln Asn His Gln Gly His Tyr Phe Ala Glu Ser Leu Thr Asp Ser Val
145                 150                 155                 160

Leu Tyr Val Ser Phe Gln Glu Leu Ala Thr Arg Ile Ser His Arg Asn
```

```
                        165                 170                 175
Thr Gly Lys Ala Cys Asn Asp Pro Val Ala Asp Gln Leu Met Ala Lys
                180                 185                 190

Ile Ser Ala Asp Glu Asn Leu His Met Ile Phe Tyr Arg Asp Val Ser
            195                 200                 205

Glu Ala Ala Phe Asp Leu Val Pro Asn Gln Ala Met Lys Ser Leu His
210                 215                 220

Leu Ile Leu Ser His Phe Gln Met Pro Gly Phe Gln Val Pro Glu Phe
225                 230                 235                 240

Arg Arg Lys Ala Val Ile Ala Val Gly Val Tyr Asp Pro Arg
                245                 250                 255

Ile His Leu Asp Glu Val Val Met Pro Val Leu Lys Lys Trp Cys Ile
                260                 265                 270

Phe Glu Arg Glu Asp Phe Thr Gly Glu Gly Ala Lys Leu Arg Asp Glu
                275                 280                 285

Leu Ala Leu Val Ile Lys Asp Leu Glu Leu Ala Cys Asp Lys Phe Glu
290                 295                 300

Val Ser Lys Gln Arg Gln Leu Asp Arg Glu Ala Arg Thr Gly Lys Lys
305                 310                 315                 320

Val Ser Ala His Glu Leu His Lys Thr Ala Gly Lys Leu Ala Met Ser
                325                 330                 335

Arg Arg (2) INFORMATION FOR SEQ ID NO: 5:

(i) SEQUENCE CHARACTERISTICS:
        (A) LENGTH: 548 base pairs
        (B) TYPE: nucleic acid
        (C) STRANDEDNESS: single
        (D) TOPOLOGY: not relevant (ii) MOLECULE TYPE: other nucleic acid
        (A) DESCRIPTION: /desc = "NUCLEIC ACID"

(xi) SEQUENCE DESCRIPTION: SEQ ID NO: 5:

GATCATCATC GGCCGGCTGC CGCGCAGGGC GCCGACACCG GCGAGTGCGG GCGCGAGGAT      60

CGGCCCCCAC CAGTTCGGCA GCTGCGTGTC GATGCGCTCC ACAATCCCGG GAAACAGCT     120

GACCATTACC TCCTCAATAT GAGCCTCGAA AAACTTGCCG CTGTGCGCGG CGTCGTGGT     180

AGCGCACACA ACAACTGTTA GCTGACCAGC AGGATCGGCG CTCTTACCGG TCTGTTCAC     240

GCATATCTGA ACGGACGGCT GGGAGCCACC CGCAAGCAAT TCATCGACTA CTGCGTCAA     300

ATGTTGCTCA GCACCGCCGC CACCTACGCA CCGCACCGCG AGCGGGGAGA ATCCGAACA     360

TCCATCCCAG CCGGGCCGCA CAACTGAGGA CGACTGGGGT TCACCCCACG CGGCCACCG     420

GGCCCGCCGA TGCCAGCATC CTGCCCGCTG CTGGCAGCTC AACATGCCGC GCGAAGCCC     480

AACTTGATGC TACCGAGAGA CACAGATATA TTGACTGCAA CCATTAGACA CAGATAACT     540

GAGGCGCC                                                            548

(2) INFORMATION FOR SEQ ID NO: 6:

(i) SEQUENCE CHARACTERISTICS:
        (A) LENGTH: 52 amino acids
        (B) TYPE: amino acid
        (C) STRANDEDNESS: not relevant
        (D) TOPOLOGY: not relevant (ii) MOLECULE TYPE: peptide
```

(xi) SEQUENCE DESCRIPTION: SEQ ID NO: 6:

Glu Phe Tyr Lys Phe Leu Phe Thr Phe Leu Ala Met Ala Glu Lys Leu
1               5                   10                  15

Val Asn Phe Asn Ile Asp Glu Leu Val Thr Ser Phe Glu Ser His Asp
            20                  25                  30

Ile Asp His Tyr Tyr Thr Glu Gln Lys Ala Met Glu Asn Val His Gly
        35                  40                  45

Glu Thr Tyr Ala
50

(2) INFORMATION FOR SEQ ID NO: 7:

(i) SEQUENCE CHARACTERISTICS:
        (A) LENGTH: 52 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 7:

Ile Phe Ile Ser Asn Leu Lys Tyr Gln Thr Leu Leu Asp Ser Ile Gln
1               5                   10                  15

Gly Arg Ser Pro Asn Val Ala Leu Leu Pro Leu Ile Ser Ile Pro Glu
            20                  25                  30

Leu Glu Thr Trp Val Glu Thr Trp Ala Phe Ser Glu Thr Ile His Ser
        35                  40                  45

Arg Ser Tyr Thr
50

(2) INFORMATION FOR SEQ ID NO: 8:

(i) SEQUENCE CHARACTERISTICS:
        (A) LENGTH: 52 amino acids
        (B) TYPE: amino acid
        (C) STRANDEDNESS: not relevant
        (D) TOPOLOGY: not relevant (ii) MOLECULE TYPE: peptide (xi) SEQUENCE DESCRIPTION: SEQ ID NO: 8:

Glu Thr Met Lys Val Val Ser Asn Phe Leu Glu Val Gly Glu Tyr Asn
1               5                   10                  15

Ala Ile Ala Ala Thr Gly Met Leu Trp Asp Ser Ala Gln Ala Ala Glu
            20                  25                  30

Gln Lys Asn Gly Tyr Leu Ala Gln Val Leu Asp Glu Ile Arg His Thr
        35                  40                  45

His Gln Cys Ala
50

(2) INFORMATION FOR SEQ ID NO: 9:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Glu Thr Met Lys Val Ile Ser Asn Phe Leu Glu Val Gly Glu Tyr Asn
1               5                   10                  15

```
Ala Ile Ala Ala Ser Ala Met Leu Trp Asp Ser Ala Thr Ala Ala Glu
            20                  25                  30

Gln Lys Asn Gly Tyr Leu Ala Gln Val Leu Asp Glu Ile Arg His Thr
        35                  40                  45

His Gln Cys Ala
    50
```

(2) INFORMATION FOR SEQ ID NO: 10:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Asn Ala Leu Lys Leu Phe Leu Thr Ala Val Ser Pro Leu Glu Tyr Gln
1               5                   10                  15

Ala Phe Gln Gly Phe Ser Arg Val Gly Arg Gln Phe Ser Gly Ala Gly
            20                  25                  30

Ala Arg Val Ala Cys Gln Met Gln Ala Ile Asp Glu Leu Arg His Val
        35                  40                  45

Gln Thr Gln Val
    50
```

(2) INFORMATION FOR SEQ ID NO: 11:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Ser Thr Leu Lys Ser His Tyr Gly Ala Ile Ala Val Gly Glu Tyr Ala
1               5                   10                  15

Ala Val Thr Gly Glu Gly Arg Met Ala Arg Phe Ser Lys Ala Pro Gly
            20                  25                  30

Asn Arg Asn Met Ala Thr Phe Gly Met Met Asp Glu Leu Arg His Gly
        35                  40                  45

Gln Leu Gln Leu
    50
```

(2) INFORMATION FOR SEQ ID NO: 12:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Leu Val Gly Asp Met Ile Thr Glu Glu Ala Leu Pro Thr Tyr Gln Thr
1               5                   10                  15

Met Leu Asn Thr Leu Asp Gly Val Arg Asp Glu Thr Gly Ala Ser Pro
            20                  25                  30
```

```
Thr Ser Trp Ala Ile Trp Thr Arg Ala Trp Thr Ala Glu Glu Asn Arg
        35                  40                  45

His Gly Asp Leu Leu Asn
 50

(2) INFORMATION FOR SEQ ID NO: 13:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Pro
            20                  25                  30

Thr Pro Trp Ala Ile Trp Thr Arg Ala Trp Thr Ala Glu Glu Asn Arg
        35                  40                  45

His Gly Asp Leu Leu Asn
 50

(2) INFORMATION FOR SEQ ID NO: 14:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Leu Val Gly Asp Met Ile Thr Glu Glu Ala Leu Pro Thr Tyr Gln Thr
 1               5                  10                  15

Met Leu Asn Thr Leu Asp Gly Val Arg Asp Glu Thr Gly Ala Ser Leu
            20                  25                  30

Thr Pro Trp Ala Val Trp Thr Arg Ala Trp Thr Ala Glu Glu Asn Arg
        35                  40                  45

His Gly Asp Leu Leu His
 50

(2) INFORMATION FOR SEQ ID NO: 15:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Leu Val Gly Asp Met Ile Thr Glu Glu Ala Leu Pro Thr Tyr Gln Thr
 1               5                  10                  15

Met Leu Asn Thr Leu Asp Gly Ala Lys Asp Glu Thr Gly Ala Ser Pro
            20                  25                  30

Thr Ser Trp Ala Val Trp Thr Arg Ala Trp Thr Ala Glu Glu Asn Arg
        35                  40                  45

His Gly Asp Leu Leu Asn
```

(2) INFORMATION FOR SEQ ID NO: 16:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Leu Val Gly Asp Met Ile Thr Glu Glu Ala Leu Pro Thr Tyr Gln Thr
1               5                   10                  15
Met Leu Asn Thr Leu Asp Gly Val Arg Asp Glu Thr Gly Ala Ser Pro
            20                  25                  30
Thr Ser Trp Ala Ile Trp Thr Arg Ala Trp Thr Ala Glu Glu Asn Arg
        35                  40                  45
His Gly Asp Leu Leu Asn
    50
```

(2) INFORMATION FOR SEQ ID NO: 17:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Leu Ile Gly Asp Met Ile Thr Glu Glu Ala Leu Pro Thr Tyr Gln Thr
1               5                   10                  15
Met Ile Asn Thr Leu Asp Gly Val Arg Asp Glu Thr Gly Ala Thr Val
            20                  25                  30
Thr Pro Trp Ala Ile Trp Thr Arg Ala Trp Thr Ala Glu Glu Asn Arg
        35                  40                  45
His Gly Asp Leu Leu Asn
    50
```

(2) INFORMATION FOR SEQ ID NO: 18:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Leu Val Gly Asp Met Ile Thr Glu Glu Ala Leu Pro Thr Tyr Gln Thr
1               5                   10                  15
Met Leu Asn Thr Leu Asp Gly Val Arg Asp Glu Thr Gly Ala Ser Leu
            20                  25                  30
Thr Pro Trp Ala Ile Trp Thr Arg Ala Trp Thr Ala Glu Glu Asn Arg
        35                  40                  45
His Gly Asp Leu Leu Asn
    50
```

(2) INFORMATION FOR SEQ ID NO: 19:

(i) SEQUENCE CHARACTERISTICS:
            (A) LENGTH: 54 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 19:

Leu Val Gly Asp Met Ile Thr Glu Glu Ala Leu Pro Thr Tyr Met Ser
1               5                   10                  15

Met Leu Asn Arg Cys Asp Gly Ile Lys Asp Asp Thr Gly Ala Gln Pro
                20                  25                  30

Thr Ser Trp Ala Thr Trp Thr Arg Ala Trp Thr Ala Glu Glu Asn Arg
            35                  40                  45

His Gly Asp Leu Leu Asn
    50

(2) INFORMATION FOR SEQ ID NO: 20:

(i) SEQUENCE CHARACTERISTICS:
            (A) LENGTH: 54 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 20:

Ser Asp Val Ala Gln Val Ala Met Val Gln Asn Leu Val Thr Glu Asp
1               5                   10                  15

Asn Leu Pro Ser Tyr His Arg Glu Ile Ala Met Asn Met Gly Met Asp
                20                  25                  30

Gly Ala Trp Gly Gln Trp Val Asn Arg Trp Thr Ala Glu Glu Asn Arg
            35                  40                  45

His Gly Ile Ala Leu Arg
    50

(2) INFORMATION FOR SEQ ID NO: 21:

(i) SEQUENCE CHARACTERISTICS:
            (A) LENGTH: 52 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 21:

Glu Lys Ile Leu Val Phe Leu Leu Ile Glu Gly Ile Phe Phe Ile Ser
1               5                   10                  15

Ser Phe Tyr Ser Ile Ala Leu Leu Arg Val Arg Gly Leu Met Pro Gly
                20                  25                  30

Ile Cys Leu Ala Asn Asn Tyr Ile Ser Arg Asp Glu Leu Leu His Thr
            35                  40                  45

Arg Ala Ala Ser
    50

(2) INFORMATION FOR SEQ ID NO: 22:

(i) SEQUENCE CHARACTERISTICS:
            (A) LENGTH: 52 amino acids
            (B) TYPE: amino acid (C) STRANDEDNESS: single
            (D) TOPOLOGY: linear (ii) MOLECULE TYPE: peptide (xi) SEQUENCE DESCRIPTION: SEQ ID NO: 22:

Leu Cys Leu Met Ser Val Asn Ala Leu Glu Ala Ile Arg Phe Tyr Val
1               5                   10                  15

Ser Phe Ala Cys Ser Phe Ala Phe Ala Glu Arg Glu Leu Met Glu Gly
                20                  25                  30

Asn Ala Lys Ile Ile Arg Leu Ile Ala Arg Asp Glu Ala Leu His Leu
            35                  40                  45

Thr Gly Thr Gln
    50

(2) INFORMATION FOR SEQ ID NO: 23:

(i) SEQUENCE CHARACTERISTICS:
            (A) LENGTH: 52 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

Cys Ser Leu Asn Leu Gln Leu Val Gly Glu Ala Cys Phe Thr Asn Pro
1               5                   10                  15

Leu Ile Val Ala Val Thr Glu Trp Ala Ala Ala Asn Gly Asp Glu Ile
                20                  25                  30

Thr Pro Thr Val Phe Leu Ser Ile Glu Thr Asp Glu Leu Arg His Met
            35                  40                  45

Ala Asn Gly Tyr
    50

(2) INFORMATION FOR SEQ ID NO: 24:

(i) SEQUENCE CHARACTERISTICS:
            (A) LENGTH: 52 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 24:

Cys Ser Val Asn Leu Gln Leu Val Gly Asp Thr Cys Phe Thr Asn Pro
1               5                   10                  15

Leu Ile Val Ala Val Thr Glu Trp Ala Ile Gly Asn Gly Asp Glu Ile
                20                  25                  30

Thr Pro Thr Val Phe Leu Ser Val Glu Thr Asp Glu Leu Arg His Met
            35                  40                  45

Ala Asn Gly Tyr
    50

(2) INFORMATION FOR SEQ ID NO: 25:

(i) SEQUENCE CHARACTERISTICS:
            (A) LENGTH: 52 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 25:

Phe Leu Thr Ala Val Ser Phe Ser Phe Glu Tyr Val Leu Thr Asn Leu
1               5                   10                  15

Leu Phe Val Pro Phe Met Ser Gly Ala Ala Tyr Asn Gly Asp Met Ala
                20                  25                  30

Thr Val Thr Phe Gly Phe Ser Ala Gln Ser Asp Glu Ala Arg His Met
            35                  40                  45

Thr Leu Gly Leu
    50

(2) INFORMATION FOR SEQ ID NO: 26:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Val Ala Ile Met Leu Thr Phe Ser Phe Glu Thr Gly Phe Thr Asn Met
1               5                   10                  15

Gln Phe Leu Gly Leu Ala Ala Asp Ala Ala Glu Ala Gly Asp Tyr Thr
                20                  25                  30

Phe Ala Asn Leu Ile Ser Ser Ile Gln Thr Asp Glu Ser Arg His Ala
            35                  40                  45

Gln Gln Gly Gly
    50

(2) INFORMATION FOR SEQ ID NO: 27:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Tyr Leu Gly Phe Ile Tyr Thr Ser Phe Gln Glu Arg Ala Thr Phe Ile
1               5                   10                  15

Ser His Gly Asn Thr Ala Arg Gln Ala Lys Glu His Gly Asp Ile Lys
                20                  25                  30

Leu Ala Gln Ile Cys Gly Thr Ile Ala Ala Asp Glu Lys Arg His Glu
            35                  40                  45

Thr Ala Tyr Thr
    50

(2) INFORMATION FOR SEQ ID NO: 28:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Tyr Leu Gly Phe Ile Tyr Thr Ser Phe Gln Glu Arg Ala Thr Phe Ile

```
                1               5                  10                 15
Ser His Gly Asn Thr Ala Arg Leu Ala Lys Glu His Gly Asp Ile Lys
                    20                  25                  30

Leu Ala Gln Ile Cys Gly Thr Ile Thr Ala Asp Glu Lys Arg His Glu
                    35                  40                  45

Thr Ala Tyr Thr
         50

(2) INFORMATION FOR SEQ ID NO: 29:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Tyr Leu Gly Phe Ile Tyr Thr Ser Phe Gln Glu Arg Ala Thr Phe Val
 1               5                  10                  15

Ser His Gly Asn Thr Ala Arg His Ala Lys Asp His Gly Asp Val Lys
                    20                  25                  30

Leu Ala Gln Ile Cys Gly Thr Ile Ala Ser Asp Glu Lys Arg His Glu
                    35                  40                  45

Thr Ala Tyr Thr
         50

(2) INFORMATION FOR SEQ ID NO: 30:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Tyr Leu Gly Phe Val Tyr Thr Ser Phe Gln Glu Arg Ala Thr Phe Val
 1               5                  10                  15

Ser His Gly Asn Ser Ala Arg Leu Ala Lys Glu His Gly Asp Leu Lys
                    20                  25                  30

Met Ala Gln Ile Cys Gly Ile Ile Ala Ser Asp Glu Lys Arg His Glu
                    35                  40                  45

Thr Ala Tyr Thr
         50

(2) INFORMATION FOR SEQ ID NO: 31:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Tyr Leu Gly Phe Ile Tyr Thr Ser Phe Gln Glu Arg Ala Thr Phe Ile
 1               5                  10                  15

Ser His Gly Asn Thr Ala Arg Gln Ala Lys Glu His Gly Asp Leu Lys
                    20                  25                  30
```

Leu Ala Gln Ile Cys Gly Thr Ile Ala Ala Asp Glu Lys Arg His Glu
            35                  40                  45

Thr Ala Tyr Thr
        50

(2) INFORMATION FOR SEQ ID NO: 32:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Tyr Leu Gly Phe Val Tyr Thr Ser Leu Arg Lys Gly Val Thr Phe Val
1               5                   10                  15

Ser His Gly Asn Thr Ala Arg Leu Ala Lys Glu His Gly Asp Met Lys
            20                  25                  30

Leu Ala Gln Ile Cys Gly Ser Ile Ala Ala Asp Glu Lys Arg His Glu
            35                  40                  45

Thr Ala Tyr Thr
        50

(2) INFORMATION FOR SEQ ID NO: 33:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Tyr Leu Gly Phe Ile Tyr Thr Ser Phe Gln Glu Arg Ala Thr Phe Ile
1               5                   10                  15

Ser His Gly Asn Thr Ala Arg Leu Ala Lys Asp His Gly Asp Met Lys
            20                  25                  30

Leu Ala Gln Ile Cys Gly Ile Ile Ala Ala Asp Glu Lys Arg His Glu
            35                  40                  45

Thr Ala Tyr Thr
        50

(2) INFORMATION FOR SEQ ID NO: 34:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Tyr Met Gly Phe Ile Tyr Thr Ser Phe Gln Glu Arg Ala Thr Phe Ile
1               5                   10                  15

Ser His Ala Asn Thr Ala Lys Leu Ala Gln His Tyr Gly Asp Lys Asn
            20                  25                  30

Leu Ala Gln Val Cys Gly Asn Ile Ala Ser Asp Glu Lys Arg His Ala
            35                  40                  45

(2) INFORMATION FOR SEQ ID NO: 35:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Thr Asp Ser Val Leu Tyr Val Ser Phe Gln Glu Leu Ala Thr Arg Ile
1               5                   10                  15

Ser His Arg Asn Thr Gly Lys Ala Cys Asn Asp Pro Val Ala Asp Gln
            20                  25                  30

Leu Met Ala Lys Ile Ser Ala Asp Glu Asn Leu His Met Ile Phe Tyr
            35                  40                  45

Arg
```

(2) INFORMATION FOR SEQ ID NO: 36:

(i) SEQUENCE CHARACTERISTICS:
        (A) LENGTH: 1600 base pairs
        (B) TYPE: nucleic acid
        (C) STRANDEDNESS: not relevant
        (D) TOPOLOGY: not relevant (ii) MOLECULE TYPE: other nucleic acid
        (A) DESCRIPTION: /desc = "NUCLEIC ACID"

(ix) FEATURE:
        (A) NAME/KEY: CDS
        (B) LOCATION: 549..1562

(xi) SEQUENCE DESCRIPTION: SEQ ID NO: 36:

```
GATCATCATC GGCCGGCTGC CGCGCAGGGC GCCGACACCG GCGAGTGCGG GCGCGAGGAT    60

CGGCCCCCAC CAGTTCGGCA GCTGCGTGTC GATGCGCTCC ACAATCCCGG GAAACAGCTC   120

GACCATTACC TCCTCAATAT GAGCCTCGAA AAACTTGCCG CTGTGCGCGG CGTCGTGGTG   180

AGCGCACACA ACAACTGTTA GCTGACCAGC AGGATCGGCG CTCTTACCGG TCTGTTCACC   240

GCATATCTGA ACGGACGGCT GGGAGCCACC CGCAAGCAAT TCATCGACTA CTGCGTCAAC   300

ATGTTGCTCA GCACCGCCGC CACCTACGCA CCGCACCGCG AGCGGGGAGA ATCCGAACAC   360

TCCATCCCAG CCGGGCCGCA CAACTGAGGA CGACTGGGGT TCACCCCACG CGGCCACCGG   420

CGCCCGCCGA TGCCAGCATC CTGCCCGCTG CTGGCAGCTC AACATGCCGC GCGAAGCCCA   480

AACTTGATGC TACCGAGAGA CACAGATATA TTGACTGCAA CCATTAGACA CAGATAACTG   540

GAGGCGCC ATG TCA GCC AAG CTG ACC GAC CTG CAG CTG CTG CAC GAA CTT   590
         Met Ser Ala Lys Leu Thr Asp Leu Gln Leu Leu His Glu Leu
             340                 345                 350

GAA CCG GTC GTC GAG AAG TAC CTG AAC CGG CAC CTG AGC ATG CAC AAG   638
Glu Pro Val Val Glu Lys Tyr Leu Asn Arg His Leu Ser Met His Lys
        355                 360                 365

CCC TGG AAC CCG CAC GAC TAC ATC CCG TGG TCG GAC GGG AAG AAC TAC   686
Pro Trp Asn Pro His Asp Tyr Ile Pro Trp Ser Asp Gly Lys Asn Tyr
    370                 375                 380

TAC GCG CTC GGC GGG CAG GAT TGG GAC CCC GAC CAG AGC AAG CTT TCT   734
Tyr Ala Leu Gly Gly Gln Asp Trp Asp Pro Asp Gln Ser Lys Leu Ser
385                 390                 395                 400
```

```
GAT GTC GCC CAG GTG GCG ATG GTG CAG AAC CTG GTC ACC GAG GAC AAC      782
Asp Val Ala Gln Val Ala Met Val Gln Asn Leu Val Thr Glu Asp Asn
                    405                 410                 415

CTG CCG TCG TAT CAC CGC GAG ATC GCG ATG AAC ATG GGC ATG GAC GGC      830
Leu Pro Ser Tyr His Arg Glu Ile Ala Met Asn Met Gly Met Asp Gly
                420                 425                 430

GCG TGG GGG CAG TGG GTC AAC CGT TGG ACC GCC GAG GAG AAT CGG CAC      878
Ala Trp Gly Gln Trp Val Asn Arg Trp Thr Ala Glu Glu Asn Arg His
            435                 440                 445

GGC ATC GCG CTG CGC GAC TAC CTG GTG GTG ACC CGA TCG GTC GAC CCT      926
Gly Ile Ala Leu Arg Asp Tyr Leu Val Val Thr Arg Ser Val Asp Pro
        450                 455                 460

GTC GAG TTG GAG AAA CTT CGC CTC GAG GTA GTC AAC CGG GGC TTC AGC      974
Val Glu Leu Glu Lys Leu Arg Leu Glu Val Val Asn Arg Gly Phe Ser
465                 470                 475                 480

CCA GGC CAA AAC CAC CAG GGC CAC TAT TTC GCG GAG AGC CTC ACC GAC     1022
Pro Gly Gln Asn His Gln Gly His Tyr Phe Ala Glu Ser Leu Thr Asp
                    485                 490                 495

TCC GTC CTC TAT GTC AGT TTC CAG GAA CTG GCA ACC CGG ATT TCG CAC     1070
Ser Val Leu Tyr Val Ser Phe Gln Glu Leu Ala Thr Arg Ile Ser His
                500                 505                 510

CGC AAT ACC GGC AAG GCA TGT AAC GAC CCC GTC GCC GAC CAG CTC ATG     1118
Arg Asn Thr Gly Lys Ala Cys Asn Asp Pro Val Ala Asp Gln Leu Met
            515                 520                 525

GCC AAG ATC TCG GCA GAC GAG AAT CTG CAC ATG ATC TTC TAC CGC GAC     1166
Ala Lys Ile Ser Ala Asp Glu Asn Leu His Met Ile Phe Tyr Arg Asp
        530                 535                 540

GTC AGC GAG GCC GCG TTC GAC CTC GTG CCC AAC CAG GCC ATG AAG TCG     1214
Val Ser Glu Ala Ala Phe Asp Leu Val Pro Asn Gln Ala Met Lys Ser
545                 550                 555                 560

CTG CAC CTG ATT TTG AGC CAC TTC CAG ATG CCC GGC TTC CAA GTA CCC     1262
Leu His Leu Ile Leu Ser His Phe Gln Met Pro Gly Phe Gln Val Pro
                    565                 570                 575

GAG TTC CGG CGC AAA GCC GTG GTC ATC GCC GTC GGG GGT GTC TAC GAC     1310
Glu Phe Arg Arg Lys Ala Val Val Ile Ala Val Gly Gly Val Tyr Asp
                580                 585                 590

CCG CGC ATC CAC CTC GAC GAA GTC GTC ATG CCG GTA CTG AAG AAA TGG     1358
Pro Arg Ile His Leu Asp Glu Val Val Met Pro Val Leu Lys Lys Trp
            595                 600                 605

TGT ATC TTC GAG CGC GAG GAC TTC ACC GGC GAG GGG GCT AAG CTG CGC     1406
Cys Ile Phe Glu Arg Glu Asp Phe Thr Gly Glu Gly Ala Lys Leu Arg
        610                 615                 620

GAC GAG CTG GCC CTG GTG ATC AAG GAC CTC GAG CTG GCC TGC GAC AAG     1454
Asp Glu Leu Ala Leu Val Ile Lys Asp Leu Glu Leu Ala Cys Asp Lys
625                 630                 635                 640

TTC GAG GTG TCC AAG CAA CGC CAA CTC GAC CGG GAA GCC CGT ACG GGC     1502
Phe Glu Val Ser Lys Gln Arg Gln Leu Asp Arg Glu Ala Arg Thr Gly
                    645                 650                 655

AAG AAG GTC AGC GCA CAC GAG CTG CAT AAA ACC GCT GGC AAA CTG GCG     1550
Lys Lys Val Ser Ala His Glu Leu His Lys Thr Ala Gly Lys Leu Ala
                660                 665                 670

ATG AGC CGT CGT TAGCCCGGCG ACGATGCAGA GCGCGCAGCG CGATGAGC           1600
Met Ser Arg Arg
            675

(2) INFORMATION FOR SEQ ID NO: 37:

(i) SEQUENCE CHARACTERISTICS:
        (A) LENGTH: 338 amino acids
        (B) TYPE: amino acid
        (D) TOPOLOGY: linear
```

(ii) MOLECULE TYPE: protein (xi) SEQUENCE DESCRIPTION: SEQ ID NO: 37:

```
Met Ser Ala Lys Leu Thr Asp Leu Gln Leu Leu His Glu Leu Glu Pro
 1               5                  10                  15
Val Val Glu Lys Tyr Leu Asn Arg His Leu Ser Met His Lys Pro Trp
                20                  25                  30
Asn Pro His Asp Tyr Ile Pro Trp Ser Asp Gly Lys Asn Tyr Tyr Ala
             35                  40                  45
Leu Gly Gly Gln Asp Trp Asp Pro Asp Gln Ser Lys Leu Ser Asp Val
         50                  55                  60
Ala Gln Val Ala Met Val Gln Asn Leu Val Thr Glu Asp Asn Leu Pro
 65                  70                  75                  80
Ser Tyr His Arg Glu Ile Ala Met Asn Met Gly Met Asp Gly Ala Trp
                 85                  90                  95
Gly Gln Trp Val Asn Arg Trp Thr Ala Glu Glu Asn Arg His Gly Ile
                100                 105                 110
Ala Leu Arg Asp Tyr Leu Val Val Thr Arg Ser Val Asp Pro Val Glu
            115                 120                 125
Leu Glu Lys Leu Arg Leu Glu Val Val Asn Arg Gly Phe Ser Pro Gly
        130                 135                 140
Gln Asn His Gln Gly His Tyr Phe Ala Glu Ser Leu Thr Asp Ser Val
145                 150                 155                 160
Leu Tyr Val Ser Phe Gln Glu Leu Ala Thr Arg Ile Ser His Arg Asn
                165                 170                 175
Thr Gly Lys Ala Cys Asn Asp Pro Val Ala Asp Gln Leu Met Ala Lys
            180                 185                 190
Ile Ser Ala Asp Glu Asn Leu His Met Ile Phe Tyr Arg Asp Val Ser
        195                 200                 205
Glu Ala Ala Phe Asp Leu Val Pro Asn Gln Ala Met Lys Ser Leu His
        210                 215                 220
Leu Ile Leu Ser His Phe Gln Met Pro Gly Phe Gln Val Pro Glu Phe
225                 230                 235                 240
Arg Arg Lys Ala Val Ile Ala Val Gly Gly Val Tyr Asp Pro Arg
                245                 250                 255
Ile His Leu Asp Glu Val Val Met Pro Val Leu Lys Lys Trp Cys Ile
            260                 265                 270
Phe Glu Arg Glu Asp Phe Thr Gly Glu Gly Ala Lys Leu Arg Asp Glu
        275                 280                 285
Leu Ala Leu Val Ile Lys Asp Leu Glu Leu Ala Cys Asp Lys Phe Glu
        290                 295                 300
Val Ser Lys Gln Arg Gln Leu Asp Arg Glu Ala Arg Thr Gly Lys Lys
305                 310                 315                 320
Val Ser Ala His Glu Leu His Lys Thr Ala Gly Lys Leu Ala Met Ser
                325                 330                 335
Arg Arg
```

DESATURASE ANTIGEN OF MYCOBACTERIUM TUBERCULOSIS

This is a division of application Ser. No. 08/917,299, filed Jul. 25, 1997, now U.S. Pat. No. 6,010,855 which claims the benefit of U.S. Provisional Appln. No. 60/022,713, filed Jul. 26, 1996, all of which are incorporated herein by reference.

BACKGROUND OF THE INVENTION

Tuberculosis and leprosy, caused by the bacilli from the *Mycobacterium tuberculosis* complex and *M. leprae* respectively are the two major mycobacterial diseases. Pathogenic mycobacteria have the ability to survive within host phagocytic cells. From the interactions between the host and the bacteria results the pathology of the tuberculosis infection through the damages the host immune response causes on tissues (Andersen & Brennan, 1994). Alternatively, the protection of the host is also dependent on its interactions with mycobacteria.

Identification of the bacterial antigens involved in these interactions with the immune system is essential for the understanding of the pathogenic mechanisms of mycobacteria and the host immunological response in relation to the evolution of the disease. It is also of great importance for the improvement of the strategies for mycobacterial disease control through vaccination and immunodiagnosis.

Through the years, various strategies have been followed for identifying mycobacterial antigens. Biochemical tools for fractionating and analysing bacterial proteins permitted the isolation of antigenic proteins selected on their capacity to elicit B or T cell responses (Romain et al., 1993; Sorensen et al., 1995). The recent development of molecular genetic methods for mycobacteria (Jacobs et al., 1991; Snapper et al., 1990; Hatful, 1993; Young et al., 1985) allowed the construction of DNA expression libraries of both *M. tuberculosis* and *M. leprae* in the λgt11 vector and their expression in *E. coli*. The screening of these recombinant libraries using murine polyclonal or monoclonal antibodies and patient sera led to the identification of numerous antigens (Braibant et al., 1994; Hermans et al., 1995; Thole & van der Zee, 1990). However, most of them turned out to belong to the group of highly conserved heat shock proteins (Thole & van der Zee, 1990; Young et al., 1990).

The observation in animal models that specific protection against tuberculosis was conferred only by administration of live BCG vaccine, suggested that mycobacterial secreted proteins might play a major role in inducing protective immunity. These proteins were shown to induce cell mediated immune responses and protective immunity in guinea pig or mice model of tuberculosis (Pal & Horwitz, 1992; Andersen, 1994; Haslov et al., 1995). Recently, a genetic methodology for the identification of exported proteins based on PhoA gene fusions was adapted to mycobacteria by Lim et al. (1995). It permitted the isolation of *M. tuberculosis* DNA fragments encoding exported proteins. Among them, the already known 19 kDa lipoprotein (Lee et al., 1992) and the ERP protein similar to the *M. leprae* 28 kDa antigen (Berthet et al., 1995).

SUMMARY OF THE INVENTION

We have characterized a new *M. tuberculosis* exported protein named DES identified by using the PhoA gene fusion methodology. The des gene, which seems conserved among mycobacterial species, encodes an antigenic protein highly recognized by human sera from both tuberculosis and leprosy patients but not by sera from tuberculous cattle. The amino acid sequence of the DES protein contains two sets of motifs that are characteristical of the active sites of enzymes from the class II diiron-oxo protein family. Among this family, the DES protein presents significant homologies to soluble stearoyl-ACP desaturases.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

The invention will be further clarified by the following examples, which are intended to be purely exemplary of the invention.

Bacteria, media and growth conditions

The bacterial strains and plasmids used in this study are listed in FIG. 8 *E. coli* DH5α or BL21(DE3)pLysS cultures were routinely grown in Luria B medium (Difco) at 37° C. Mycobacterium cultures were grown in Middlebrook 7H9 medium (Difco) supplemented with Tween 0.05%, glycerol (0.2%) and ADC (glucose, 0.2% BSA fraction V, 0.5%; and NaCl, 0.085%) at 37° C. Antibiotics when required were added at the following concentrations: ampicillin (100 μg/ml), kanamycin (20 μg/ml).

Human and cattle sera

Serum specimens from 20 individuals with pulmonary or extra-pulmonary tuberculosis (*M. tuberculosis* infected) were obtained from the Bligny sanatorium (France), 6 sera from *M. bovis* infected human tuberculous patients and 24 sera from BCG-vaccinated patients suffering from other pathologies were respectively obtained from Institut Pasteur, (Madagascar), and the Centre de Biologie Médicale spécialisée (CBMS) (Institut Pasteur, Paris). Sera from tuberculous cattle (*M. bovis* infected) were obtained from CNEVA, (Maison Alfort).

Subcloning procedures

Restriction enzymes and T4 DNA ligase were purchased from Gibco/BRL, Boehringer Mannheim and New England Biolabs. All enzymes were used in accordance with the manufacturer's recommendations. A 1-kb ladder of DNA molecular mass markers was from Gibco/BRL. DNA fragments used in the cloning procedures were gel purified using the Geneclean II kit (BIO 101 Inc., La Jolla, Calif.). Cosmids and plasmids were isolated by alkaline lysis (Sambrook et al., 1989). Bacterial strains were transformed by electroporation using the Gene Pulser unit (Bio-Rad Laboratories, Richmond, Calif.).

BRIEF DESCRIPTION OF THE DRAWINGS

FIG. 2 shows the nucleotide and derived amino acid sequences of the *M. tuberculosis* des gene.

FIG. 3 shows a comparative sequence analysis of class II diiron-oxo proteins and the *M. tuberculosis* Des protein. Shaded residues indicate cluster ligands and probable iron ligands in the *M. tuberculosis* Des protein. Bold unshaded framed letters are probable residues involved in the network of hydrogen bonds to the cluster. Other bold letters indicate conserved residues that are believed to participate in the $O_2$-binding site. Gaps introduced into the sequence of Des are indicated by dots. Accession numbers are as follows: V015555, Epstein-Barr virus ribonucleotide reductase; M58499, *Methylococcus capsulatus* methane monooxygenase hydroxylase; M60276, Pseudomonas sp. strain CF 600 phenol hydroxylase dmpN polypeptide; M59857, *Ricinus communis* stearoyl-ACP desaturase; and D38753, *O. sativa* stearoyl-ACP desaturase.

FIG. 7 shows the nucleotide and derived amino acid sequence of the *Mycoplasma tuberculosis* des gene. The underlined sequences correspond to the −35 and −10 boxes of the promoter and a Shine Dalgarno sequence that corresponds to the putative ribosomal attachment site, respectively. The adenosine labelled "+1" correspond to the transcription initiation site.

FIG. 8 is a table of the bacterial strains and plasmids used in this application.

Southern blot analysis and colony hybridization

Figure 1:
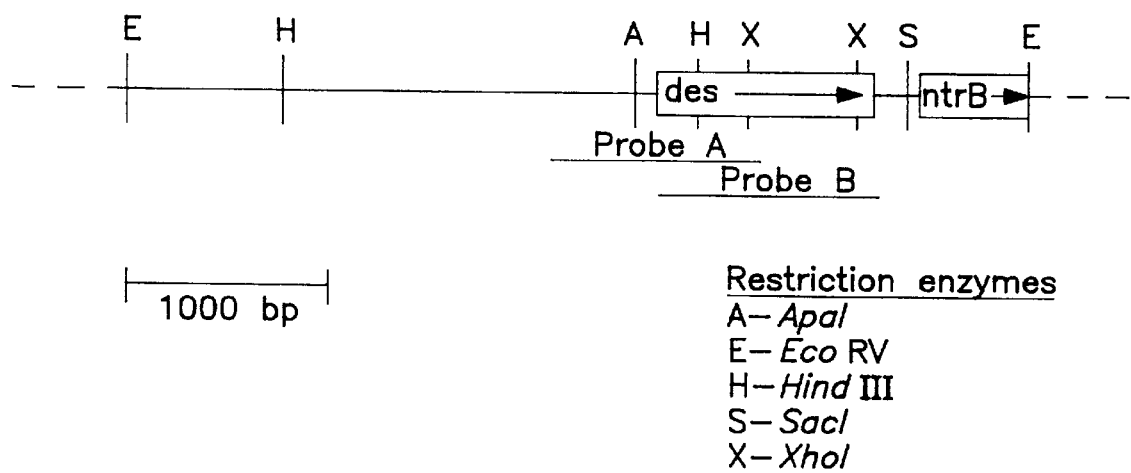
FIG. 1 is a restriction map of the 4.5 kb EcoRV fragment encoding the *M. tuberculosis* des gene.

DNA fragments for radiolabeling were separated on 0.7% agarose gels (Gibco BRL) in a Tris-borate-EDTA buffer system (Sambrook et al., 1989) and isolated from the gel by using Geneclean II (BIO 101). Radiolabeling was carried out with the random primed labeling kit Megaprime (Amersham) with 5 µCi of ($\alpha$-$^{32}$P)dCTP, and nonincorporated label was removed by passing through a Nick Column (Pharmacia). Southern blotting was carried out in 0.4 M NaOH with nylon membranes (Hybond-N+, Amersham) according to the Southern technique (Southern, 1975), prehybridization and hybridization was carried out as recommended by the manufacturer using RHB buffer (Amersham). Washing a 65° C. was as follows: two washes with 2×SSPE (150 mM NaCl, 8.8 mM $NaH_2PO_4$, 1 mM EDTA pH 7.4)—SDS 0.1% of 15 minutes each, one wash with 1×SSPE-SDS 0.1% for 10 minutes, two washes with 0.7×SSPE-SDS 0.1% of 15 minutes each. Autoradiographs were prepared by exposure with X-ray film (Kodak X-Omat AR) at −80° C. overnight. Colony hybridization was carried out using nylon membrane discs (Hybond-N+ 0.45 µm, Amersham). *E. coli* colonies adsorbed on the membranes were lysed in a (0.5M NaOH, 1.5M NaCl) solution, before being placed for one minute in a micro-wave oven to fix the DNA. Hybridization and washings were as described for the Southern blotting analysis.

DNA sequencing and analysis

Sequences of double-stranded plasmid DNA were determined by the dideoxy-chain termination method (Sanger et al., 1977) using the Taq Dye Deoxy Terminator Cycle sequencing Kit (Applied Biosystems), on a GeneAmp PCR System 9600 (Perkin Elmer), and run on a DNA Analysis System-Model 373 stretch (Applied Biosystems). The sequence was assembled and processed using DNA strider™ (CEA, France) and the University of Wisconsin Genetics Computer Group (UWGCG) packages. The BLAST algorithm (Altschul et al., 1990) was used to search protein data bases for similarity.

Expression and purification of the DES protein in *E. coli*

A 1043 bp NdeI-BamHI fragment of the des gene was amplified by PCR using nucleotides JD8 (5'-CGGCATATGTCAGCCAAGCTGACCGACCTGCAG-3') and JD9 (5'-CCGGGATCCCGCGCTCGCCGCTCTGCATCGTCG-3'), and cloned into the NdeI-BamHI sites of pET14b (Novagen) to generate pET-des. PCR amplifications were carried out in a DNA thermal Cycler (Perkin Elmer), using Taq polymerase (Cetus) according to the manufacturer's recommendations. PCR consisted of one cycle of denaturation (95° C., 6 min) followed by 25 cycles of amplification consisting of denaturation (95° C., 1 min) annealing (57° C., 1 min), and primer extension (72° C., 1 min). In the pET-des vector, the expression of the des gene is under control of the T7 bacteriophage promoter and the DES antigen is expressed as a fusion protein containing six histidine residues. Expression of the des gene was induced by addition of 0.4 mM IPTG in the culture medium. The DES protein was purified by using a nickel-chelate affinity resin according to the recommendations of the supplier (Qiagen, Chatsworth, Calif.). Linked to the localization of the DES protein in cytoplasmic inclusion bodies, the purification was carried out under denaturing conditions in guanidine hydrochloride, buffers. The protein was eluted in buffer A (6 M guanidine hydrochloride, 0.1 M $NaH_1PO_4$, 0.001 M Tris, pH 8) containing 100 mM EDTA. The purified protein was kept and used in buffer A, as all attempts to solubilize it in other buffers were unsuccessful.

SDS-PAGE and immunoblotting

Sodium dodecyl sulfate-polyacrylamide gel electrophoresis (SDS-PAGE) was carried out as described by Laemmli (1970). For Western blotting experiments (immunoblotting), approximately 10 µg of DES purified protein were run on a SDS-polyacrylamide gel and transferred onto nitrocellulose membranes (Hybond C extra, Amersham) using a Bio-Rad mini transblot apparatus according to the recommendations of the manufacturer (Bio-Rad Laboratories, Richmond, Calif.). Transfer yield was visualized by transient staining with Ponceau Rouge. The membrane were incubated with human patient or cattle sera diluted $\frac{1}{200}^e$ at 37° C. for 1 hour and with a goat anti-human (Promega) or rabbit anti-cattle (Biosys) IgG alkaline phosphatase-conjugated secondary antibody diluted $\frac{1}{2500}^e$ for 30 minutes at 37° C. The color reaction was performed by addition of 5-bromo-4-chloro-3-indolylphosphate (0.165 mg/ml) and toluidinum nitroblue tetrazolium (0.33 mg/ml) as substrates.

ELISA

The human or cattle sera were tested for antibodies against DES by enzyme-linked immunosorbent assay (ELISA). The 96-well micro-titer trays (Nunc) were coated with 0.1 µg (per well) of purified DES protein in guanidine hydrochloride buffer A (6 M guanidine hydrochloride, 0.1 M $NaH_2PO_4$, 0.01 M Tris, pH 8) (1 h at 37° C. and 16 h at 4° C.). After three washes, wells were saturated with bovine serum albumin 3% in phosphate buffered saline (PBS) for 30 mn at room temperature. After three washes, sera diluted from $\frac{1}{50}^e$ to $\frac{1}{3200}^e$ in buffer (PBS, 0.1% Tween 20, 1% bovine serum albumin) were added to the wells for 2 h at 37° C. After three washes, the wells were treated with goat anti-human IgG-alkaline phosphatase conjugate (Promega) diluted 1/4000$^c$ for 1 h at 37° C. Then, 4 mg of p-nitrophenylphosphate per ml were added as substrate. After 20 mn of incubation at 37° C., the plates were read photometrically at an optical density of 405 nm in micro-ELISA Autoreader (Dynatech, Marnes la Coquette, France).

Statistics

Antibody response of the different sera tested were compared by using the Student t test. P≧0.05 was considered nonsignificant.

Nucleotide sequence and accession number

The nucleotide sequences of des has been deposited in the Genome Sequence Data Base (GSDB) under the accession number U49839.

Cloning of the des gene

The construction of a library of fusions of *M. tuberculosis* genomic DNA to the phoA gene and its expression in *M. smegmatis*, described by Lim et al. (1995), led to the isolation of several PhoA$^+$ clones. pExp421 is the plasmid harboured by one of the PhoA$^+$ clones selected from this library. Detection of enzymatically active alkaline phosphatase indicated that the pExp421 insert contains functional expression and exportation signals. Restriction analysis showed that pExp421 carries a 1.1 kb insert. Partial determination of its sequence identified a 577 bp ORF, named des, fused in frame to the phoA gene and presenting two motifs, of 9 and 14 amino acids, conserved with soluble stearoyl-acyl-carrier protein desaturases (Lim et al., 1995). To isolate the full-length des gene, the *M. tuberculosis* H37Rv pYUB18 genomic cosmid library (Jacobs et al., 1991), was screened by colony hybridization with the 1.1 kb probe (probe A, see FIG. 1). Two hybridizing cosmids named C$_3$ and C$_4$ were selected for further isolation of the gene. C$_3$ and C$_4$ were cut with several restriction enzymes and subjected to Southern blot analysis using the 1.1 kb fragment as a probe.

The EcoRV restriction profile revealed a single hybridizing fragment of 4.5 kb which was subcloned into pBluescript KS$^-$ (Sratagene) to give plasmid pBS-des.

Characterization of the des gene

The DNA sequence of the full des ORF was determined (FIG. 2). The des gene was shown to cover a 1017 bp region, encoding a 339 amino acid protein with a calculated molecular mass of 37 kDa. The ORF starts with a potential ATG start codon at position 549, and ends with a TAG stop codon at position 1565. There is a potential Shine-Dalgarno motif (GGAGG) at position −8 upstream of the ATG. The G+C content of the ORF (62%) is consistent with the global GC content observed in mycobacterial genome. The nucleotide and deduced amino acid sequences of the des gene were compared to sequences in databases. They showed very high homologies to the *M. leprae* aadX gene located on cosmid B2266, deposited in GenBank as part of the *M. leprae* genome sequencing project (GenBank accession number no. U15182). Within the coding region, the DNA sequences were 79% identical while the encoded proteins were 80% identical (88% including conserved residues). The des gene also scored significantly against soluble stearoyl-ACP desaturases: 44% identity at the nucleotide level, 30% identity (51% including conserved residues) at the amino acid level, to the *Oryza sativa* stearoyl-ACP desaturase (accession no. D38753).

Although the detection of a phoA enzymatical activity in the *M. smegmatis* clone harbouring the pExp421 suggests the DES protein is exported, no structural similarities were found between the DES protein N terminal amino acids and signal sequences of bacterial exported proteins (Izard & Kendall, 1994).

Like in *M. leprae* genome, a second ORF presenting high homologies to the *M. leprae* putative NtrB gene (cosmid B2266), is located downstream of the des gene in *M. tuberculosis* FIG. 2. Interestingly, the two ORF, des and "NtrB", are separated in *M. tuberculosis* by two direct repeats of 66 nucleotides overlapping on 9 nucleotides (FIG. 2). Although *M. leprae* and *M. tuberculosis* seem to share the same genomic organization in this part of the chromosome, these repeats are absent from the *M. leprae* genome.

The des protein presents the conserved amino acid motifs of the class II diiron-oxo proteins Further analysis of the amino-acid sequence of the DES protein revealed the presence of conserved motifs found only in class II diiron-oxo proteins (Fox et al., 1994) (FIG. 3). These proteins are oxo-bridged diiron clusters (Fe—O—Fe) containing proteins. They possess in their secondary structure 4 alpha helices involved in the protein-derived cluster ligands. As revealed by X-ray structure studies, in these proteins, the diiron axis is oriented parallel to the long axis of the four helix bundle with ligands arising from four noncontiguous helices, B, C, E and F. *M. tuberculosis* DES protein appears to have the same active site residues as the class II diiron-oxo enzymes. This includes Glu and His residues ($E_{107}$ and $H_{110}$ in helix C, $E_{167}$ in helix E and $E_{197}$ and $H_{200}$ in helix F) that are ligands to the iron atoms, Asp, Glu and Arg residues ($E_{106}$ and $R_{109}$ in helix C, $D_{196}$ in helix F) that are involved in a hydrogen-bonding network to the cluster and, Ile and Thr residues that may be part of the O$_2$-binding site ($T_{170}$ in helix E, $I_{193}$ in helix F). Thus, the *M. tuberculosis* DES protein contains in its primary sequence two conserved D/E(ENXH) motifs separated by 85 amino acids.

The class II diiron-oxo protein family contains up to date ribonucleotide reductases, hydrocarbon hydroxylases (methane monooxygenase, toluene-4-monooxygenase and phenol hydroxylase) and soluble-ACP desaturases. On the overall sequence alignment the DES protein presents higher homology to soluble stearoyl-ACP desaturases than to ribonucleotide reductases or bacterial hydroxylases. The percentage identity at the amino acid level of the DES protein was said to be 30% with the *Oryza sativa* stearoyl-ACP desaturase, whereas it is only 17% with the *Methylococcus capsulatus* methane monooxygenase (accession no.M58499), 17.5% with the Pseudomonas sp CF 600 phenol hydroxylate (accession no.M60276) and 17.7% with the Epstein Barr ribonucleotide reductase (accession no.V01555). Homologies to the soluble Δ9 desaturases mostly concern the amino acids located within the active site in helices C, E and F (FIG. 3).

Distribution of the des gene in other mycobacterial species

Figure 4:
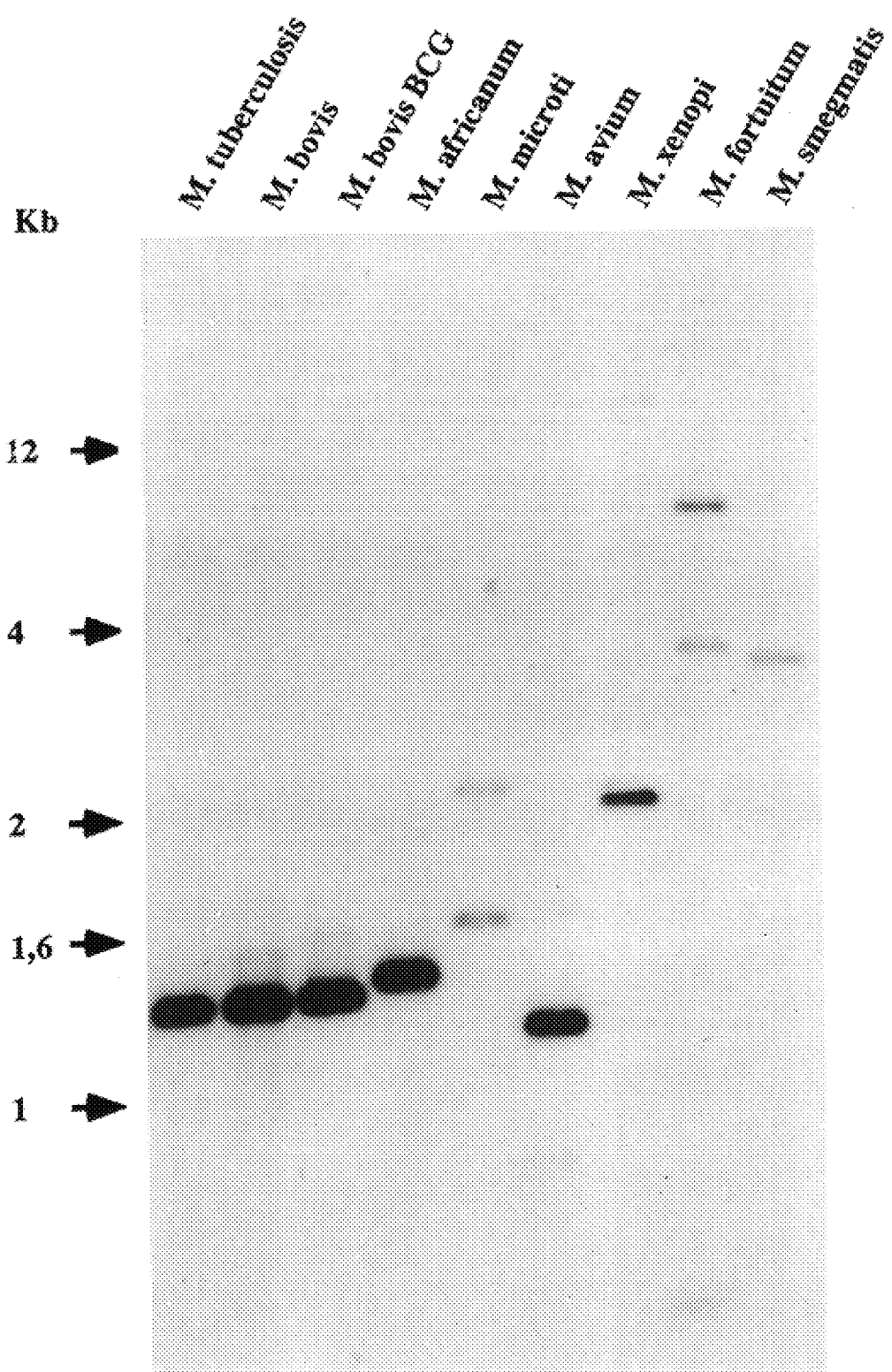
FIG. 4 is a Southern blot analysis of the distribution of the des gene in other mycobacterial species. DNA from various mycobacterial strains were PstI-digested, electrophoresed, transferred onto a nylon membrane by Southern blotting, and hybridized using probe B, which is shown in FIG. 1.

The presence of the des gene in PstI-digested chromosomal DNA from various mycobacterial strains was analyzed by Southern blotting (FIG. 4). The probe used (probe B) is a PCR amplification product corresponding to nucleotides 572 to 1589 (see FIG. 1). The probe hybridized on all mycobacterial genomic DNA tested. Strong signals were detected in *M. tuberculosis, M. bovis, M. bovis* BCG, *M. africanum* and *M. avium*. Weaker signals were visible in *M. microti, M. zenopi, M. fortuitum* and *M. smegmatis*. Thus, the des gene seems to be present in single copy at least in the slow growing *M. tuberculosis, M. bovis, M. bovis* BCG, *M. africanum, M. avium* and *M. zenopi* as well as in the fast growing *M. smegmatis*.

Expression of the des gene in *E. coli*

Figure 5:
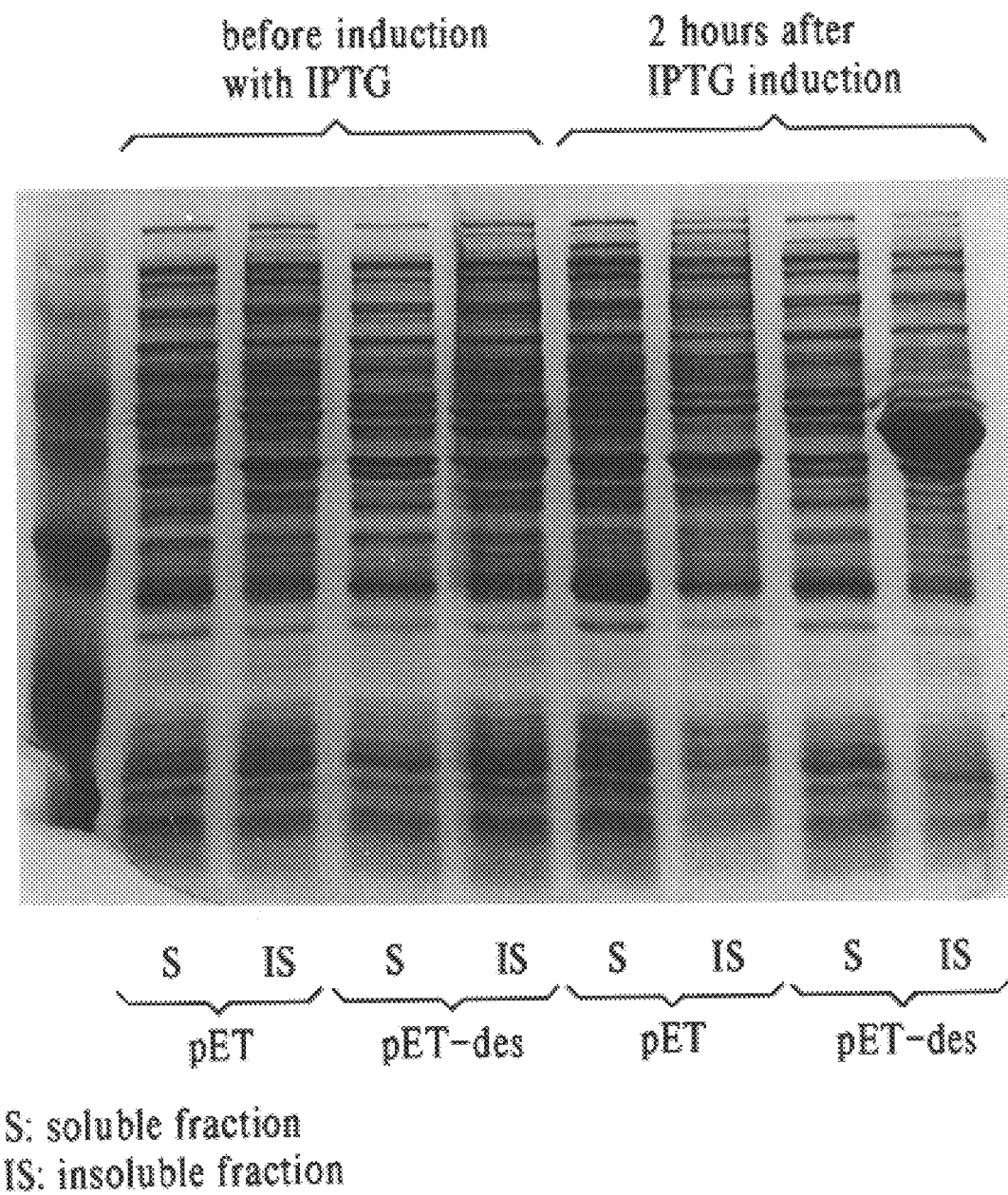
FIG. 5 shows an SDS-PAGE gel of soluble and insoluble extracts from *E. coli* expressing the DES protein on plasmid pETdes (I-1718).

In order to overexpress the DES protein, the des gene was subcloned into the bacteriophage T7 promoter-based expression vector pET14b (Novagen). A PCR amplification product of the des gene (see material and methods) was cloned into the NdeI-BamHI sites of the vector, leading to plasmid pET-des. Upon IPTG induction of *E. coli* BL21 DE3 pLysS cells harbouring the plasmid pET-des, a protein of about 40 kDa was overproduced. The size of the overproduced protein is in agreement with the molecular mass calculated from the deduced polypeptide. As shown in FIG. 5, the great majority of the overproduced DES protein is present in the insoluble matter of *E. coli* cells. This probably results from the precipitation of the over-concentrated protein in *E. coli* cytoplasm thus forming inclusion bodies. To be able to dissolve the protein, the purification was carried out using a nickel chelate affinity resin under denaturating conditions in guanidine hydrochloride buffers. Among all the conditions tested (pH, detergents . . . ), the only condition in which the protein could be eluted without precipitating in the column and remain soluble, was in a buffer containing 6 M guanidine hydrochloride.

Figure 9:
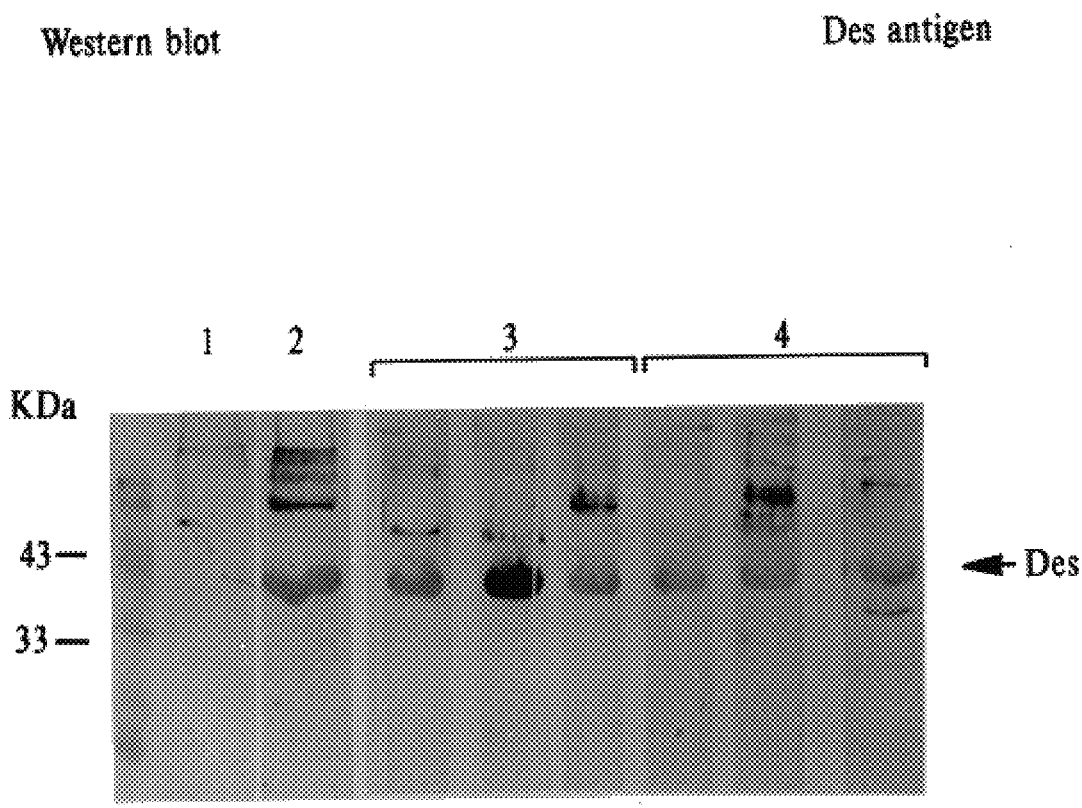
FIG. 9 is a Western blot showing the recognition of the purified DES protein by antibodies from *M. bovis* and *M. tuberculosis*-infected humans and cattle.

Immunogenicity of the DES protein after infection 20 serum samples from *M. tuberculosis* infected human patients (4 with extra-pulmonary tuberculosis, 15 with pulmonary tuberculosis and 1 with both forms if the disease), 6 sera from *M. bovis* infected human patients and 4 sera from *M. bovis* infected cattle were tested either pooled or taken individually in immunoblot experiments to determine the frequency of recognition of the purified DES protein by antibodies from infected humans or cattle. 20 out of the 20 sera from the *M. tuberculosis* infected human patients and 6 out of the 6 sera from the *M. bovis* infected human patients recognized the recombinant antigen as shown by the reaction with the 37 kDa band, (FIG. 9). Furthermore, a pool of sera from human lepromatous leprosy patients also reacted against the DES antigen.

In contrast, the pool of serum specimens from *M. bovis* infected cattle did not recognize the DES protein. These results indicate that the DES protein is highly immunogenic in tuberculosis human patients. Both pulomonary and extra-pulmonary tuberculosis patients recognize the antigen.

Magnitude of human patients antibody response

Figure 6:
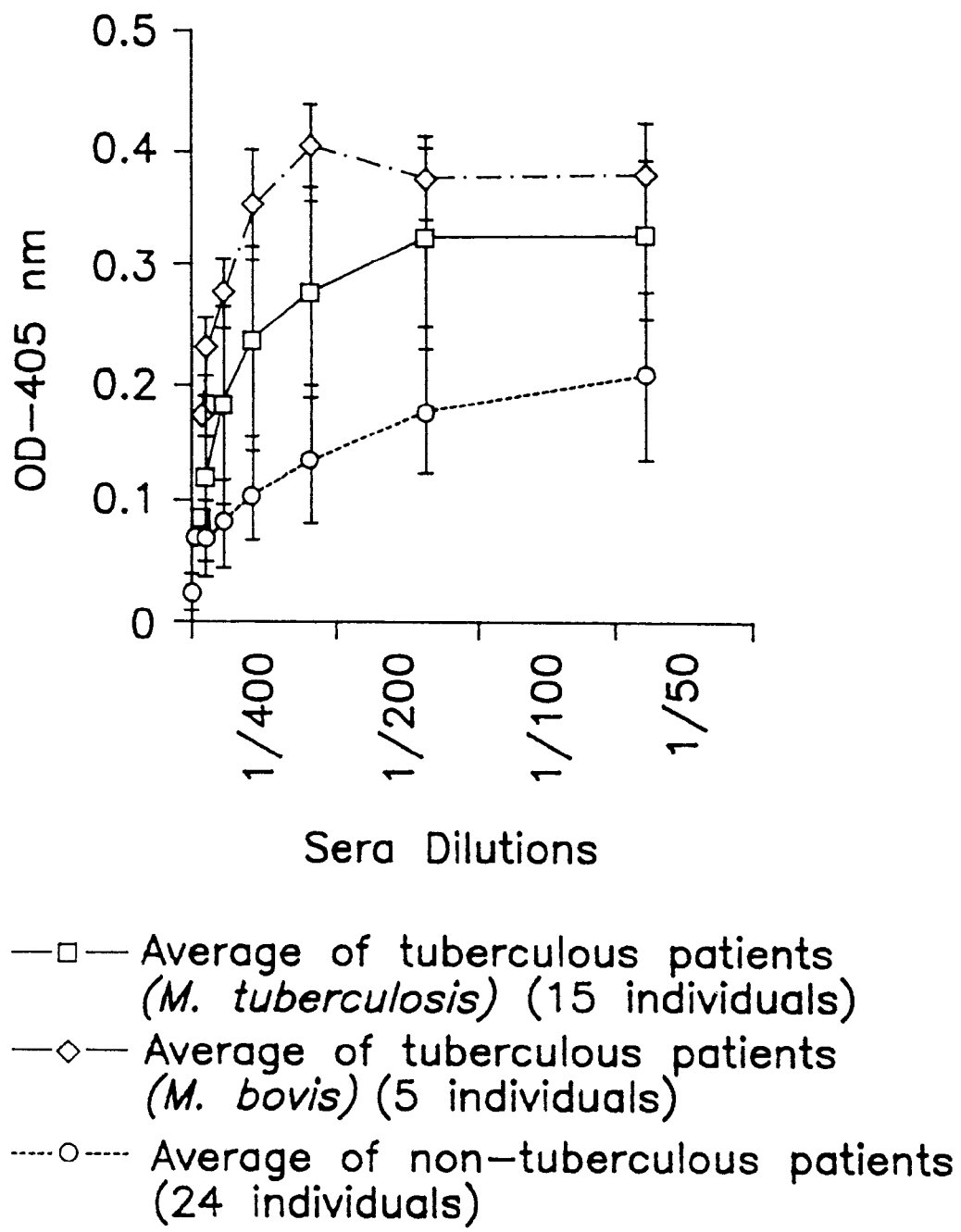
FIG. 6 shows the results of ELISAs of the sensitivity of the antibody response to the DES antigen of human tuberculous and non-tuberculous patients.

An enzyme-linked immunosorbent assay (ELISA) was used to compare the sensitivity of the different serum samples from 20 tuberculosis patients (15 infected by *M. tuberculosis* and 5 infected by *M. bovis*) to the DES antigen. This technique was also carried out to compare the sensitivity of the antibody response to DES of the 20 tuberculosis patients to the one of 24 patients (BCG-vaccinated) suffering from other pathologies. As shown on FIG. 6, patients suffering from other pathologies than tuberculosis, react at a low level to the DES antigen (average $OD_{405}$=0.17 for a serum dilution $1/100^c$). The average antibody response from the tuberculosis patients infected by *M. tuberculosis* or *M. bovis* against the same antigen is much more sensitive ($OD_{405}$=0.32 and $OD_{405}$=0.36 respectively, for a serum dilution $1/100^c$). This difference in the sensitivity of the immunological response is statistically highly significant at every dilution from $1/50^c$ to $1/3200^c$ as shown by a Student $t_{95}$ test ($t_{95}$=5.18, 6.57, 6.16, 5.79, 4.43, 2.53 and 1.95, at sera dilutions $1/50^c$, $1/100^c$, $1/200^c$, $1/400^c$, $1/800^c$, $1/1600^c$ and $1/3200^c$, respectively). No differences in the sensitivity of the antibody response was noticed between patients suffering from pulmonary or extra-pulmonary tuberculosis.

The PhoA gene fusion methodology permitted the identification of a new *M. tuberculosis* exported antigenic protein.

This 37 kDa protein contains conserved amino acid residues which are characteristical of class II diiron-oxo-proteins. Proteins from that family are all enzymes that require iron for activity. They include ribonucleotide reductases, hydrocarbon hydoxylases and stearoyl-ACP desaturases. The *M. tuberculosis* DES protein only presents significant homologies to plant stearoyl-ACP desaturases (44% identity at the nucleotide level, and 30% identity at the amino-acid level) which are also exported enzymes as they are translocated across the chloroplastic membranes (Keegstra & Olsen, 1989). This result suggests that the DES protein could be involved in the mycobacterial fatty acid biosynthesis. Furthermore, the localization of the protein outside the cytoplasm would be consistent with its role in the lipid metabolism, since lipids represent 60% of the cell wall constituents and that part of the biosynthesis of the voluminous mycolic acids containing 60 to 90 carbon atoms occurs outside the cytoplasm. Among all the different steps of the lipid metabolism, desaturation reactions are of special interest, first because they very often take place at early steps of lipid biosynthesis and secondly because, through the control they have on the unsaturation rate of membranes, they contribute to the adaptation of mycobacteria to their environment (Wheeler & Ratledge, 1994). An enzyme system involving a stearoyl-Coenzyme A desaturase (analog of the plant stearoyl-ACP-desaturases), catalyzing oxydative desaturation of the CoA derivatives of stearic and palmitic acid to the corresponding $\Delta 9$ monounsaturated fatty acids has been biochemically characterized in *Mycobacterium phlei* (Fulco & Bloch, 1962; Fulco & Bloch, 1964; Kashiwabara et al., 1975; Kashiwabara & Sato, 1973). This system was shown to be firmly bound to a membranous structure (Fulco & Bloch, 1964). Thus, *M. tuberculosis* stearoyl-Coenzyme A desaturase ($\Delta 9$ desaturase) is expected to be an exported protein. Sonicated extracts of *E. coli* expressing the DES protein were assayed for $\Delta 9$ desaturating activity according to the method described by Legrand and Bensadoun (1991), using (stearoyl-CoA) $^{14}C$ as a substrate. However, no $\Delta 9$ desaturating activity could be detected. This result is probably linked to the fact desaturation systems are multi-enzyme complexes involving electron transport chains and numerous cofactors, often difficult to render functional in vitro. *E. coli* and mycobacteria being very different from a lipid metabolism point of view, the *M. tuberculosis* recombinant $\Delta 9$ desaturase might not dipose in *E. coli* of all the cofactors and associated enzymes required for activity or might not interact properly with them. Moreover, not all cofactors involved in the $\Delta 9$ desaturation process of mycobacteria are known, and they might be missing in the incubation medium.

However, if the DES protein exceeds a $\Delta 9$ desaturase, an amazing point concerns its primary sequence. Indeed, all animal, fungal and the only two bacterial $\Delta 9$ desaturases sequenced to date (Sakamoto et al., 1994) are integral membrane proteins which have been classified into a third class of diiron-oxo proteins on the basis of their primary sequences involving histidine conserved residues (Shanklin et al., 1994). The plant soluble $\Delta 9$ desaturases are the only desaturases to possess the type of primary sequence of class II diiron-oxo proteins (Shanklin & Somerville, 1991). No bacteria have yet been found which have a plant type $\Delta 9$ desaturase.

As shown by immunoblotting and ELISA experiments, the DES protein is a highly immunogenic antigen which elicits B cell response in 100% of the tuberculosis *M. bovis* or *M. tuberculosis*-infected human patients tested, independent of the form of the disease (extrapulmonary or pulmonary). It also elicits an antibody response in lepromatous leprosy patients. Interestingly, although more sera would need to be tested, tuberculous cattle do not seem to recognize the DES antigen. Furthermore, the ELISA experiments showed that it is possible to distinguish tuberculosis patients from patients suffering from other pathologies on the basis of the sensitivity of their antibody response to the DES antigen. The DES antigen is therefore a good candidate to be used for serodiagnosis of the tuberculosis in human patients. The reason why the non-tuberculous patients tested recognize at a low level the DES protein could be due to the fact they are all BCG-vaccinated individuals (BCG expressing the protein), or to a cross-reactivity of their antibody response with other bacterial antigens. It would now be interesting to known whether the DES antigen possesses in addition to its B cell epitopes, T cell epitotes which are the only protective ones in the host immunological response against pathogenic mycobacteria. If the DES protein is also a good stimulator of the T cell response in a majority of tuberculosis patients, it could be used either individually or as part of a "cocktail" of antigens in the design of a subunit vaccine against tuberculosis.

The references cited herein are listed on the following pages and are expressly incorporated by reference.

Other embodiments of the invention will be apparent to those skilled in the art from consideration of the specification and practice of the invention disclosed herein. It is intended that the specification and examples be considered as exemplary on, with a true scope and spirit of the invention being indicated by the following claims.

1. Altschul, S. F., W. Gish, W. Miller, E. M. Myers, and D. J. Lipman. 1990. Basic local alignment search tool. Journal of Molecular Biology. 215:403–410.

2. Andersen, A. B., and P. Brennan. 1994. Proteins and antigens of *Mycobacterium tuberculosis*, p. 307–332. In B. R. Bloom (ed.). Tuberculosis: Pathogenesis, Protection, and Control. ASM, Washington, DC.

3. Andersen, P. 1994. Effective vaccination of mice against *Mycobacterium tuberculosis* infection with a soluble mixture of secreted mycobacterial proteins. Infect. Immun. 62:2536–2544.

4. Berthet, F. X., J. Rauzier, E. M. Lim, W. Philipp, B. Gicquel, and D. Portnoï. 1995. Characterization of the *M. tuberculosis* erp gene encoding a potential cell surface protein with repetitive structures. Microbiology. 141:2123–2130.

5. Braibant, M., L. D. Wit, P. Peirs, M. Kalai, J. Ooms, A. Drowart, K. Huygen, and J. Content. 1994. Structure of the *Mycobacterium tuberculosis* antigen 88, a protein related to the *Escherichia coli* PstA periplasmic phosphate permease subunit. Infection and Immunity, 62:849–854.

6. Fox, B. G., J. Shanklin, J. Ai, T. M. Loerh, and J. Sanders-Loerh. 1994. Resonance Raman evidence for an Fe—O—Fe center in stearoyl-ACP desaturase. Primary sequence identity with other diiron-oxo proteins. Biochemistry. 33:12776–12786.

7. Fulco, A. J., and K. Bloch. 1962. Cofactor requirements for fatty acid desaturation in *Mycobacterium phlei*. Biochim. Biophys. Acta. 63:545–546.

8. Fulco, A. J., and K. Bloch, 1964. Cofactor requirements for the formation of Δ9 unsaturated fatty acids in *Mycobacterium phlei*. The Journal of Biological Chemistry. 239:993–997.

9. Haslov, K., A. Andersen, S. Nagai, A. Gottschau, T. Sorensen, and P. Andersen. 1995. Guinea pig cellular immune responses to proteins secreted by *Mycobacterium tuberculosis*. Infection and Immunity. 63:804–810.

10. Hatfull, G. F. 1993. Genetic transformation of mycobacteria. Trends in microbiology. 1:310–314.

11. Hermans, P. W. M., F. Abebe, V. I. O. Kuteyi, A. H. J. Kolk, J. E. R. Thole, and M. Harboe. 1995. Molecular and immunological characterization of the highly conserved antigen 84 from *Mycobacterium tuberculosis* and *Mycobacterium leprae*. Infection and Immunity. 63:954–960.

12. Izard, J. W., D. A. Kendall. 1994. Signal peptides: exquisitely designed transport promoters. Molecular Microbiology. 13:765–773.

13. Jacobs, W. R., G. V. Kalpana, J. D. Cirillo, L. Pascopella, S. B. Snapper, R. A. Udani, W. Jones, R. G. Barletta, and B. R. Bloom. 1991. Genetic systems for mycobacteria. Methods enzymol. 204:537–555.

14. Kasbiwabara, Y., H. Nakagawa, G. Matsuki, and R. Sato. 1975. Effect of metal ions in the culture medium on the stearoyl-Coenzyme A desaturase activity of *Mycobacterium phlei*. J. Biochem. 78:803–810.

15. Kasbiwabara, Y., and R. Sato. 1973. Electron transfer mechanism involved in stearoyl-coenzyme A desaturation by particulate fraction of *Mycobacterium phlei*. J. Biochem. 74:405–413.

16. Keegstra, K., and L. J. Olsen. 1989. Chloroplastic precursors and their transport across the envelope membranes. Ann. Rev. Plant Physiol. Plant Mol. Biol. 40:471–501.

17. Laemmli, U.K. 1970. Cleavage of structural proteins during the assembly of the head of bacteriophage T4. Nature (London). 227:680–685.

18. Lee, B. Y., S. A. Hefta, and P. J. Brennan. 1992. Characterization of the major membrane protein of virulent *Mycobacterium tuberculosis*. Infection and Immunity. 60:2066–2074.

19. Legrand, P., and A. Bensadoun. 1991. Stearyl-CoA desaturase activity in cultured rat hepatocytes. Biochimica et Biophysica Acta. 1086:89–94.

20. Lim, E. M., J. Rauzier, J. Timm, G. Torrea, A. Murray, B. Gicquel, and D. Portnoï. 1995. Identification of *Mycobacterium tuberculosis* DNA sequences encoding exported proteins by using phoA gene fusions. Journal of Bacteriology. 177:59–65.

21. Pal, P. G., and M. A. Horwitz: 1992. Immunization with extracellular proteins of *Mycobacterium tuberculosis* induces cell-mediated immune responses and substential protective immunity in a guinea pig model of pulmonary tuberculosis. Infection and Immunity. 60:4781–4792.

22. Romain, F., A. Laqueyrerie, P. Militzer, P. Pescher, P. Chavarot, M. Lagranderie, G. Auregan, M. Gheorghiu, and G. Marchal. 1993. Identification of a *Mycobacterium bovis* BCG 45/47-kilodalton antigen complex, an immunodominant target for antibody response after immunization with living bacteria. Infection and immunity. 61:742–750.

23. Sakamoto, T., H. Wada, J. Nishida, M. Ohmori, and N. Murata. 1994. Δ9 acyl lipid desaturases of cyanobacteria. J. Biol. Chem. 269:25576–25580.

24. Sambrook, J., E. F. Fritsch, and T. Maniatis. 1989. Molecular cloning. A laboratory manual. Cold Spring Harbor Laboratory Press, Cold Spring Harbor, N.Y.

25. Sanger, F., S. Nicklen, and A. R. Coulson. 1977. DNA sequencing with chain terminating inhibitors. Proc. Natl. Acad. Sci. USA. 74:5463–5467.

26. Shanklin, J., and C. Somerville. 1991. Stearoyl-acyl-carrier-protein desaturase from higher plants is structurally unrelated to the animal and fungal homologs. Proceeding of the National Academy of Science of the United States of America. 88:2510–2514.

27. Shanklin, J., E. Whittle, and B. G. Fox. 1994. Eight histidine residues are catalytically essential in a membrane-associated iron enzyme, stearoyl-CoA desaturase, and are conserved in alkane hydroxylase and xylene monooxygenas. Biochemistry. 33:12787–12794.

28. Snapper, S. B., B. R. Bloom, and J. W. R. Jacobs. 1990. Molecular genetic approaches to mycobacterial investigation, p. 199–218. In J. McFadden (ed.), Molecular Biology of the Mycobacteria. Surrey University Press London.

29. Sorensen, A. L., S. Nagai, G. Houen, P. Andersen, and A. B. Andersen, 1995. Purification and characterization of a low-molecular-mass T-cell antigen secreted by *Mycobacterium tuberculosis*. Infection and Immunity. 63:1710–1717.

30. Southern, E. M. 1975. Detection of specific sequences among DNA fragments separated by gel electrophoresis. J. Mol. Biol. 98:503–517.

31. Studier, W., A. H. Rosenberg, J. J. Dunn, and J. W. Dubendorff. 1990. Use of T7 RNA polymerase to direct expression of cloned genes. Methods in Enzymology. 185:60–89.

32. Thole, J. E. R., and R. v. d. Zee. 1990. The 65 kD antigen: molecular studies on a ubiquitous antigen., p. 37–66. In J. McFadden (ed.). Molecular Biology of the mycobacteria. Surrey University Press, London.

33. Wheeler, P. R., and C. Ratledge. 1994. Metabolism of *Mycobacterium tuberculosis*, p. 353–385. In B. R. Bloom (ed.), Tuberculosis: Pathogenesis, Protection, and Control. ASM. Washington, DC.

34. Young, D., T. Garbe, R. Lathigra, and C. Abou-Zeid. 1990. Protein antigens: structure, function and regulation. p. 1–35. In J. McFadden (ed.), Molecular biology of mycobacteria. Surrey university Press, London.

35. Young, R. A., B. R. Bloom, C. M. Grossinsky, J. Ivany, D. Thomas, and R. W. Davis. 1985. Dissection of the *Mycobacterium tuberculosis* antigens using recombinant DNA. Proc. Natl. Acad. Sci. USA. 82:2583–2587.

What is claimed is:

1. A purified polypeptide, which is encoded by the nucleic acid sequence set forth in FIG. 2 (SEQ ID NO. 3).

2. The polypeptide according to claim 1 having an amino acid sequence comprising (SEQ ID NO. 4).

3. An immunogenic composition comprising a polypeptide according to claim 1 or 2.

* * * * *